US009441023B2

(12) United States Patent
Dock et al.

(10) Patent No.: US 9,441,023 B2
(45) Date of Patent: Sep. 13, 2016

(54) PEPTIDE YY ANALOGS

(71) Applicant: GlaxoSmithKline Intellectual Property Development Limited, Brentford, Middlesex (GB)

(72) Inventors: Steven Thomas Dock, Research Triangle Park, NC (US); Andrew James Carpenter, Research Triangle Park, NC (US); Robert Neil Hunter, III, Research Triangle Park, NC (US); Yulin Wu, Research Triangle Park, NC (US); Ved P. Srivastava, Research Triangle Park, NC (US)

(73) Assignee: GLAXOSMITHKLINE INTELLECTUAL PROPERTY DEVELOPMENT LIMITED (GB)

( * ) Notice: Subject to any disclaimer, the term of this patent is extended or adjusted under 35 U.S.C. 154(b) by 0 days.

(21) Appl. No.: 14/265,831

(22) Filed: Apr. 30, 2014

(65) Prior Publication Data
US 2014/0329742 A1 Nov. 6, 2014

Related U.S. Application Data

(60) Provisional application No. 61/816,624, filed on May 2, 2013.

(51) Int. Cl.
| | | |
|---|---|---|
| *C07K 14/575* | (2006.01) | |
| *A61K 38/26* | (2006.01) | |
| *A61K 38/22* | (2006.01) | |
| *C07K 14/47* | (2006.01) | |
| *A61K 38/55* | (2006.01) | |
| *A61K 38/17* | (2006.01) | |

(52) U.S. Cl.
CPC ........... *C07K 14/47* (2013.01); *A61K 38/1709* (2013.01); *A61K 38/26* (2013.01); *A61K 38/55* (2013.01); *C07K 14/57545* (2013.01); *A61K 38/22* (2013.01)

(58) Field of Classification Search
None
See application file for complete search history.

(56) References Cited

U.S. PATENT DOCUMENTS 7,459,432 B2 * 12/2008 Cowley et al. ................ 514/1.1
2009/0171071 A1    7/2009 Summers et al.

FOREIGN PATENT DOCUMENTS

| WO | WO-2005077094 A2 | 8/2005 |
| WO | WO-2006066024 A2 | 6/2006 |
| WO | WO-2011050008 A2 | 4/2011 |
| WO | WO-2011039096 A1 | 7/2011 |
| WO | WO-2012006566 A2 | 1/2012 |
| WO | WO-2012101413 A1 | 8/2012 |

OTHER PUBLICATIONS

Balasubramaniam et al.; Structure-Activity Studies Including a (CH2-NH) Scan of Peptide YY (PYY) Active Site, PYY(22-36), for Interaction with Rat Intestinal PYY Receptors: Development of Analogues with Potent in Vivo Activity in the Intestine; J. Med. Chem.; 2000; vol. 43, No. 18; pp. 3420-3427.
Birney et al.; GeneWise and Genomewise; Genome Research; 2004; vol. 14, No. 5; pp. 988-995.
Conlon et al.; The Primary Structure of a PYY-Related Peptide from Chicken Intestine Suggests an Anomalous Site of Cleavage of the Signal Peptide in PreproPYY; FEBS; 1992; vol. 313, No. 3; pp. 225-228.
Lerch et al.; Structural Similarities of Micelle-bound Peptide YY (PYY) and Neuropeptide Y (NPY) are Related to Their Affinity Profiles at the Y Receptors; J. Mol. Biol.; 2004; vol. 339; pp. 1153-1168.
Lindner et al.; GPC Receptors and Not Ligands Decide the Binding Mode in Neuropeptide Y Multireceptor/Multiligand System; Biochemistry; 2008; vol. 47, No. 22; pp. 5905-5914.
Medeiros et al.; Processing and Metabolism of Peptide-YY: Pivotal Roles of Dipeptidylpeptidase-IV, Aminopeptidase-P, and Endopeptidase-24.11; Endocrinology; 1994; vol. 134, No. 5; pp. 2088-2094.
Pedersen et al.; Glyco-Scan: Varying Glycosylation in the Sequence of the Peptide Hormone PYY3-36 and Its Effect on Receptor Selectivity; ChemBioChem; 2010; vol. 11; pp. 366-374.
Ensembl Transcript ENSACAT00000004946; Feb. 2012.
Ensembl Transcript ENSAMET00000020124; Feb. 2012.
Ensembl Transcript ENSCJAT00000020204; Feb. 2012.
Ensembl Transcript ENSCPOT00000025583; Feb. 2012.
Ensembl Transcript ENSDART00000052000; Feb. 2012.
Ensembl Transcript ENSDART00000128786; Feb. 2012.
Ensembl Transcript ENSEEUT00000002532; Feb. 2012.
Ensembl Transcript ENSGACT00000000592; Feb. 2012.
Ensembl Transcript ENSGACT00000013169; Feb. 2012.
Ensembl Transcript ENSGMOT00000014665; Feb. 2012.
Ensembl Transcript ENSGMOT00000019307; Feb. 2012.
Ensembl Transcript ENSLACT00000017256; Feb. 2012.
Ensembl Transcript ENSLAFT00000025898; Feb. 2012.
Ensembl Transcript ENSMMUT00000013564; Feb. 2012.
Ensembl Transcript ENSMMUT00000032446; Feb. 2012.
Ensembl Transcript ENSMODT00000015116; Feb. 2012.
Ensembl Transcript ENSMPUT00000009639; Oct. 2012.
Ensembl Transcript ENSMUST00000017455; Feb. 2012.
Ensembl Transcript ENSOANT00000030348; Feb. 2012.
Ensembl Transcript ENSOGAT00000008365; Feb. 2012.

(Continued)

*Primary Examiner* — Christina Borgeest
(74) *Attorney, Agent, or Firm* — Jason C. Fedon; William T. Han

(57) ABSTRACT

The present invention relates to novel analogs of PYY that have an improved therapeutic profile when compared to native human PYY. These novel PYY analogs are useful in the treatment of obesity, diabetes, and other disorders.

38 Claims, 2 Drawing Sheets

(56) References Cited

OTHER PUBLICATIONS

Ensembl Transcript ENSONIT00000007957; May 2012.
Ensembl Transcript ENSONIT00000025098; May 2012.
Ensembl Transcript ENSORLT00000021810; Feb. 2012.
Ensembl Transcript ENSPMAT00000008493; Feb. 2012.
Ensembl Transcript ENSPPYT00000023742; Oct. 2012.
Ensembl Transcript ENSPSIT00000014623; Jul. 2012.
Ensembl Transcript ENSPTRT00000043285; Feb. 2012.
Ensembl Transcript ENSSHAT00000017456; Feb. 2012.
Ensembl Transcript ENSSTOT00000020012; May 2012.
Ensembl Transcript ENST00000407573; Feb. 2012.
Ensembl Transcript ENSTBET00000014809; Feb. 2012.
Ensembl Transcript ENSTNIT00000003048; Feb. 2012.
Ensembl Transcript ENSTNIT00000014286; Feb. 2012.
Ensembl Transcript ENSTRUT00000027114; Feb. 2012.
Ensembl Transcript ENSTRUT00000042219; Feb. 2012.
Ensembl Transcript ENSXETT00000007337; Feb. 2012.
Ensembl Transcript ENSXMAT00000002622; Oct. 2012.
Ensembl Transcript ENSXMAT00000014664; Oct. 2012.
Ensembl Transcript ID ENSMICT00000005643; Feb. 2012.
GenBank Assembly ID GCA_000186305.1; Jul. 21, 1986.
NCBI Accession No. XP_001491077.2; Jul. 11, 2008.
Swiss-Prot Accession No. EPY88890.1; Dec. 25, 2011.
Swiss-Prot Accession No. P10082; Jan. 11, 2011.
Swiss-Prot Accession No. P10631; Jul. 1, 1989.
Swiss-Prot Accession No. P51694; Oct. 1, 1996.
Swiss-Prot Accession No. P68004; Oct. 10, 2003.
Swiss-Prot Accession No. P68005; Oct. 10, 2003.
Swiss-Prot Accession No. Q58VP8; Apr. 26, 2005.
Swiss-Prot Accession No. Q9TR93; Oct. 10, 2003.

* cited by examiner

PEPTIDE YY ANALOGS

FIELD OF THE INVENTION

This invention relates to therapeutic peptides useful in the treatment of obesity and metabolic disorders. More specifically, the invention relates to novel analogs of Peptide YY (PYY) and their use.

BACKGROUND OF THE INVENTION

The prevalence of obesity in the United States is increasing, with 35.7% of adults considered obese (BMI≥30) and 68.8% considered overweight (BMI≥25) in 2009-2010. See, for example, Flegal et al. (2012) *JAMA* 307(5):491-7. Worldwide, over 300 million people are considered obese. Obesity-related diseases, including Type 2 Diabetes Mellitus, hypertension, heart disease, joint disease, and some types of cancer have increased in prevalence as the population has grown heavier.

Prevention of obesity through diet and exercise is of critical importance to control these trends, but once patients become obese, the body's resistance to weight loss can be considerable. Diet and exercise alone may be insufficient to bring about significant weight change in severely obese patients, and both pharmacologic therapy and surgery have proven to be effective as additional aids to weight loss. Prevention and treatment of obesity are areas of high unmet medical need, with few medications currently available for chronic weight loss therapy.

Peptide YY (PYY) belongs to the PP-fold family of peptides together with pancreatic polypeptide and neuropeptide Y, which have a role in controlling appetite. See, for example, Schwartz et al. (2002) *Nature:* 418(6898):595-7. PYY is secreted as a 36 amino acid, straight chain polypeptide and then cleaved by dipeptidyl peptidase IV to produce PYY(3-36). Fasting and post-prandial concentrations of PYY in morbidly obese individuals after gastric bypass surgery are suggested as playing a role in their dramatic weight loss. See, for example, le Roux (2006) *Ann Surg.* 243(1):108-14. Peripheral infusion of PYY(3-36) has been shown to increase energy expenditure and fat oxidation rates in obese and lean subjects. See, for example, Batterham et al. (2003) *N Engl J Med.* 349(10):941-8, and Sloth et al. (2007) *Am J Physiol Endocrinol Metab.:* 293(2):E604-9. Administration of a PYY(3-36) nasal spray reduced daily caloric intake of obese individuals by 2713 kJ, resulting in a weight loss of 0.6 kg over a six-day study period. See, for example, Gantz et al. (2007) *J Clin Endocrinol Metab.* 92(5):1754-7. These results demonstrate that obese subjects retain sensitivity to PYY(3-36), in contrast to leptin, where resistance limits its therapeutic usefulness in obesity.

Accordingly, there remains a need in the art for improved PYY compositions for use in the treatment of obesity and obesity-related disorders.

BRIEF SUMMARY OF INVENTION

The present invention relates to novel analogs of PYY that have an improved therapeutic profile when compared to native human PYY. These novel PYY analogs are useful in the treatment of obesity, diabetes, and other disorders.

Briefly, in one aspect, the invention provides a polypeptide comprising the amino acid sequence:

```
                                              (SEQ ID NO: 1)
ProLysProGluXaa₁ProGlyXaa₂AspAlaSerXaa₃GluGluXaa₄

Xaa₅Xaa₆TyrTyrAlaXaa₇LeuArgXaa₈TyrXaa₉AsnTrpXaa₁₀

ThrArgGlnArgTyr
``` or a salt thereof, wherein:
$Xaa_1$ is Ala, His, or Ser;
$Xaa_2$ is Glu or Lys;
$Xaa_3$ is Pro or Ala;
$Xaa_4$ is Leu or Trp;
$Xaa_5$ is Asn, Ala, or Thr;
$Xaa_6$ is Arg or Lys;
$Xaa_7$ is Ser, Asp, or Ala;
$Xaa_8$ is His or Lys;
$Xaa_9$ is Leu or Ile; and
$Xaa_{10}$ is Val or Leu.

In another aspect, the invention provides a polypeptide selected from the group consisting of:

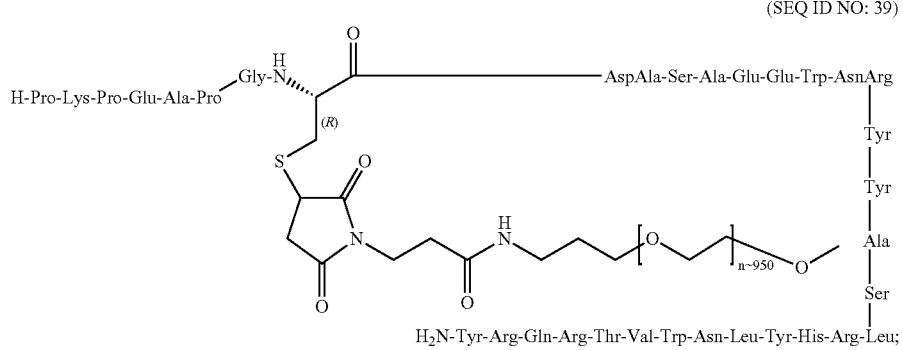

(SEQ ID NO: 39)

(SEQ ID NO: 40)
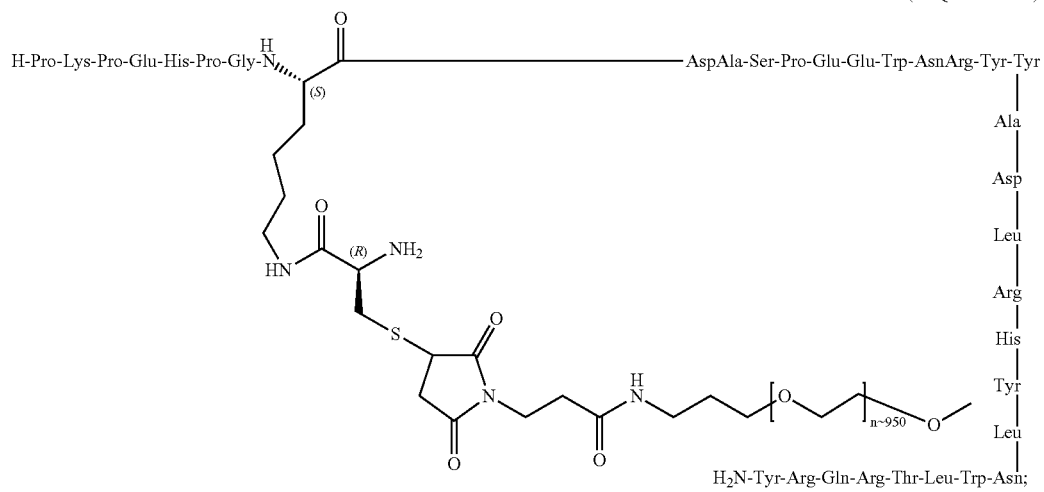
(SEQ ID NO: 41)
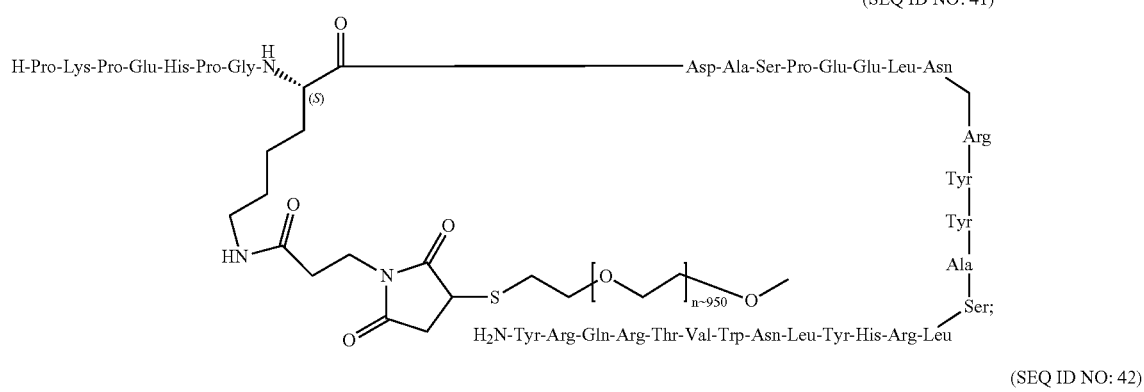
(SEQ ID NO: 42)
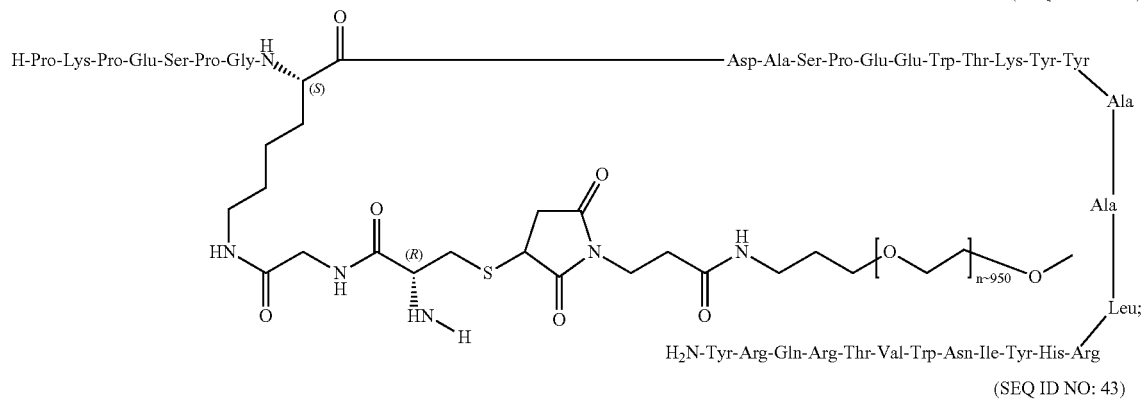
(SEQ ID NO: 43)
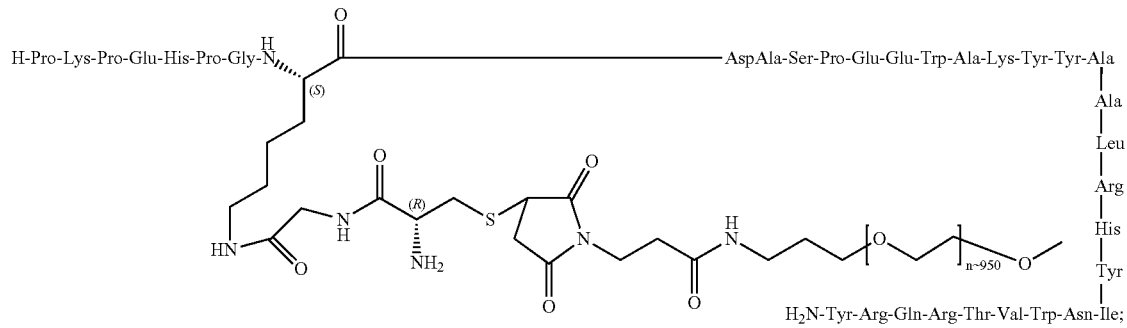

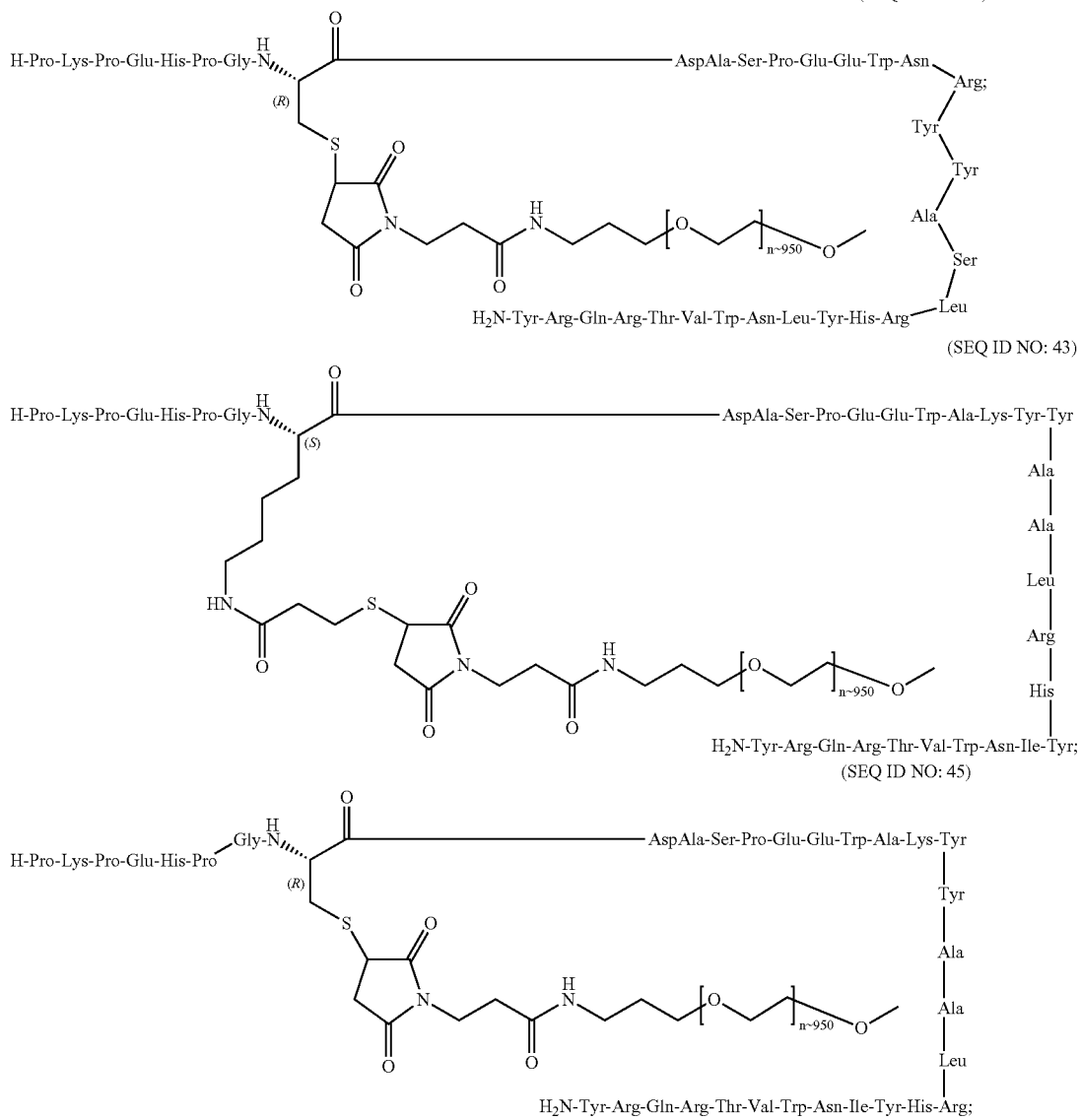

and salts thereof.

In another aspect, the invention provides a nucleic acid molecule encoding a polypeptide of the invention In yet another aspect, the invention includes an expression vector comprising a nucleic acid molecule encoding a polypeptide of the invention.

In a further aspect, the invention encompasses a host cell containing an expression vector comprising a nucleic acid molecule encoding a polypeptide of the invention.

In another aspect, the invention provides a pharmaceutical combination comprising a novel PYY polypeptide of the invention and exendin-4.

In yet another aspect, the invention provides a pharmaceutical combination comprising a novel PYY polypeptide of the invention and GLP-1.

In an additional aspect the invention provides a pharmaceutical composition comprising a novel PYY polypeptide of the invention and one or more pharmaceutically acceptable excipients.

In a further aspect, the invention encompasses a method of treating a metabolic disorder or obesity, the method comprising administering a novel PYY polypeptide or pharmaceutical combination of the invention to a subject in need thereof.

The invention also provides the use of a polypeptide or pharmaceutical combination of the invention in the preparation of a medicament for use in the treatment of obesity.

In addition, the invention provides a polypeptide or pharmaceutical combination of the invention for use in the treatment of a metabolic disorder or obesity.

DETAILED DESCRIPTION OF THE INVENTION

Figure 1:
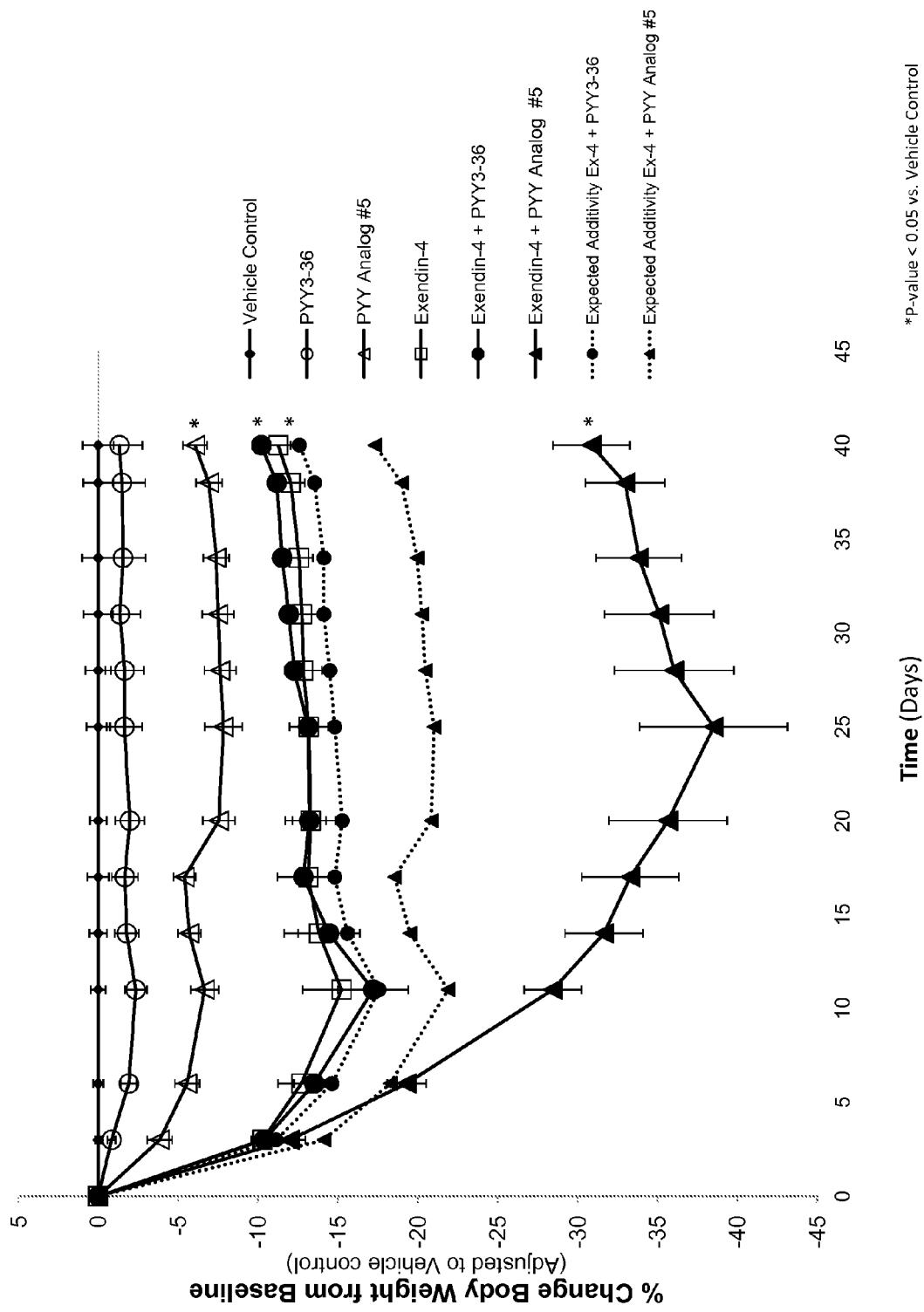
FIG. 1 shows the effects of the peptide shown in Example 5 (Analog #5), PYY(3-36)NH$_2$(PYY3-36), and exendin-4 singly and in combination on changes in body weight in diet-induced obese (DIO) Long Evans (LE) rats.

The invention provides novel analogs of PYY that have an improved therapeutic profile when compared to native human PYY. The novel PYY analogs of the invention show improved effects on food intake when compared with the native PYY sequence.

In one aspect, the novel PYY analogs comprise the amino acid sequence:

(SEQ ID NO: 1)
ProLysProGluXaa$_1$ProGlyXaa$_2$AspAlaSerXaa$_3$GluGluXaa$_4$
Xaa$_5$Xaa$_6$TyrTyrAlaXaa$_7$LeuArgXaa$_8$TyrXaa$_9$AsnTrpXaa$_{10}$
ThrArgGlnArgTyr or a salt thereof, wherein:
Xaa$_1$ is Ala, His, or Ser;
Xaa$_2$ is Glu or Lys;
Xaa$_3$ is Pro or Ala;
Xaa$_4$ is Leu or Trp;
Xaa$_5$ is Asn, Ala, or Thr;
Xaa$_6$ is Arg or Lys;
Xaa$_7$ is Ser, Asp, or Ala;
Xaa$_8$ is His or Lys;
Xaa$_9$ is Leu or Ile; and
Xaa$_{10}$ is Val or Leu.

The novel polypeptides of the invention show a statistically significant increase in the reduction of food intake in either a lean and/or diet-induced obesity animal model when compared with human PYY(3-36). Preferably the polypeptides of the invention reduce the intake of food in a lean and/or diet-induced obesity animal model by at least 20%, at least 30%, or at least 40%. More preferably, the polypeptides reduce the intake of food in a lean and/or diet-induced obesity animal model by at least 50%.

In another aspect, the invention provides a polypeptide selected from the group consisting of:

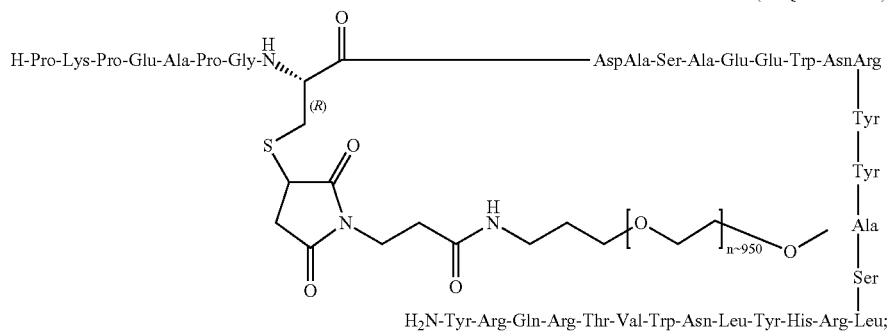

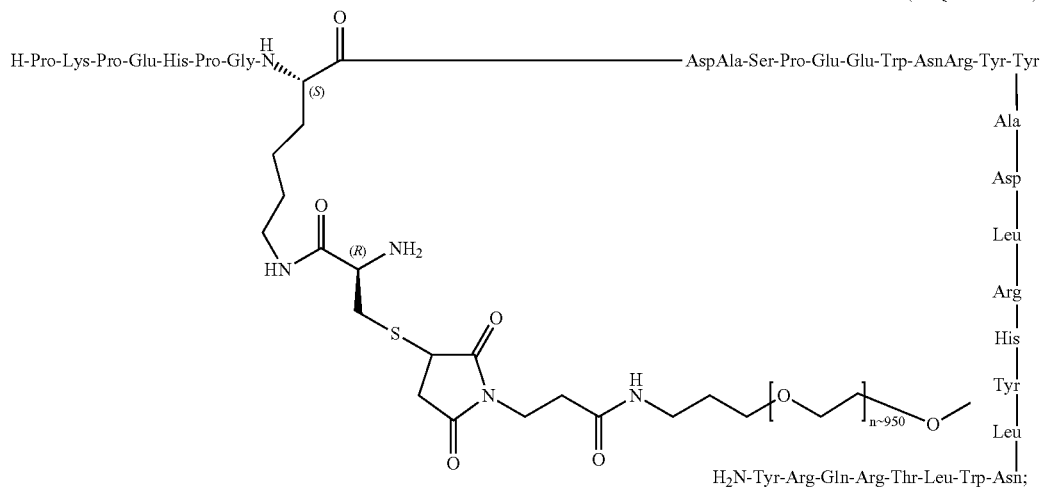

-continued
(SEQ ID NO: 41)
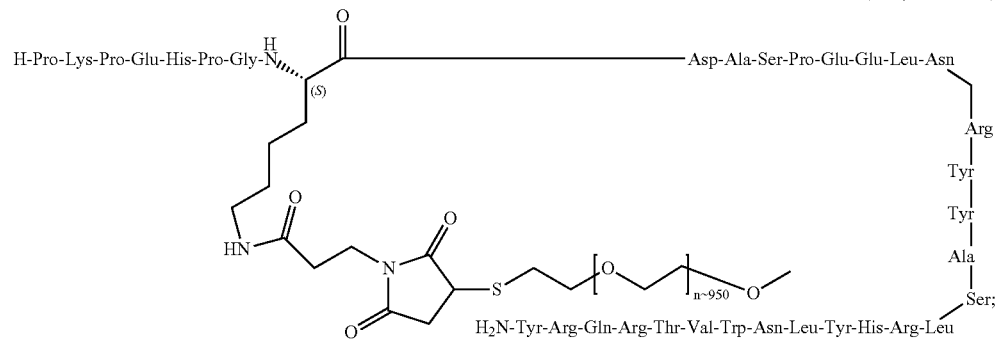
(SEQ ID NO: 42)
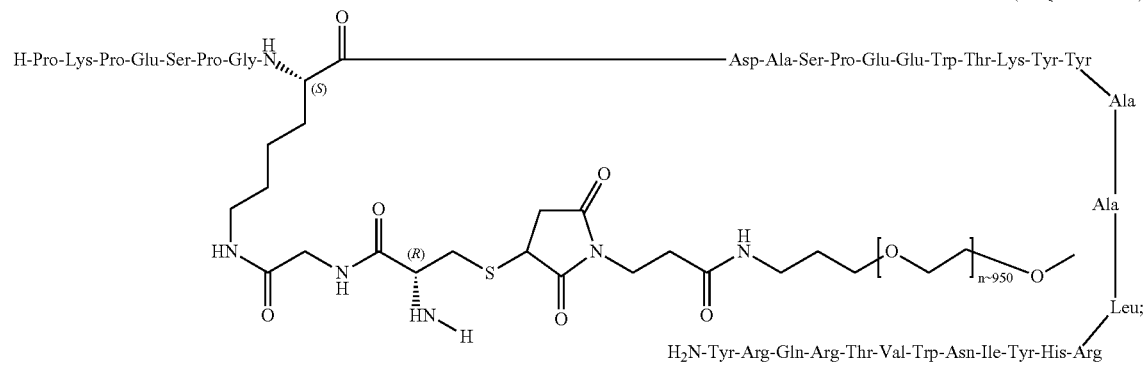
(SEQ ID NO: 43)
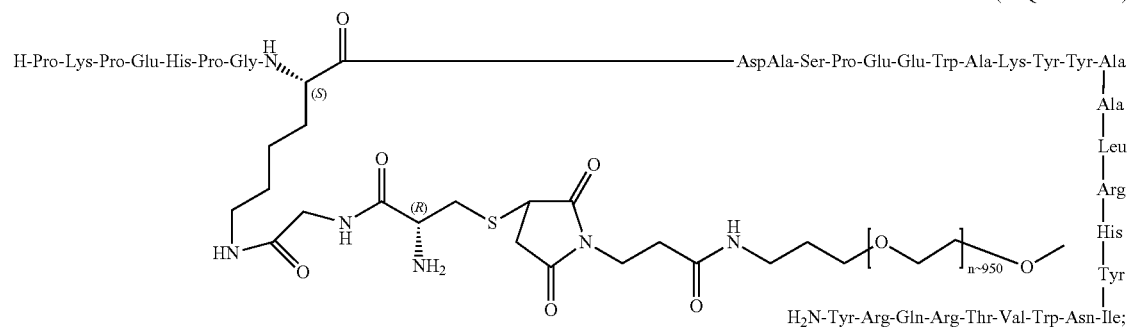
(SEQ ID NO: 44)
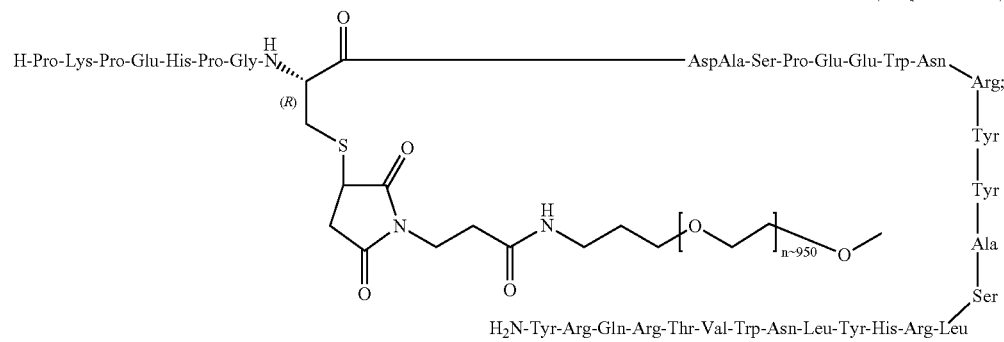

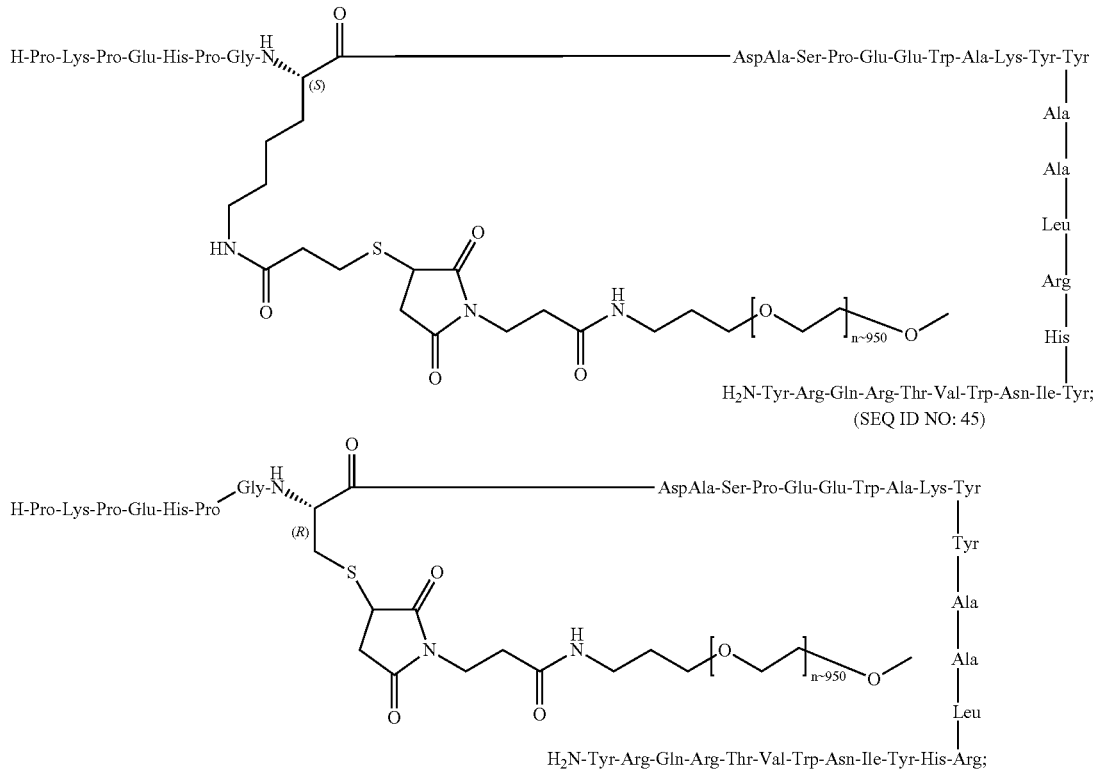

and salts thereof.

Unless otherwise indicated, the polypeptides of the invention may have either a carboxamide or carboxylic acid at the end of the amino acid chain.

The invention encompasses salts of the recited polypeptides, including pharmaceutically acceptable salts. Examples of such salts include, but are not limited to, including inorganic and organic acids and bases, including but not limited to, sulfuric, citric, maleic, acetic, oxalic, hydrochloride, hydrobromide, hydroiodide, nitrate, sulfate, bisulfite, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Also included are salts formed with free amino groups such as, for example, hydrochloric, phosphoric, acetic, trifluoroacetic, oxalic, and tartaric acids. Also included are salts that may form with free carboxy groups such as, for example sodium, potassium, ammonium, sodium, lithium, calcium, ferric hydroxides, isopropylamine, triethylamine, 2-ethylamino ethanol, histidine, and procaine salts.

The polypeptides of the invention may be prepared using standard recombinant expression or chemical peptide synthesis techniques known in the art. See, for example, Chan, Weng C., and Peter D. White, eds. *Fmoc Solid Phase Peptide Synthesis: A Practical Approach*. New York: Oxford UP, 2000, and Howl, John, ed. *Peptide Synthesis and Applications* (*Methods in Molecular Biology*). Totowa, N.J.: Humana, 2005.

The compositions and pharmaceutical combinations of the invention are useful for the treatment of metabolic disorders including, for example, hyperglycemia, impaired glucose tolerance, beta cell deficiency, diabetes (including type 1 diabetes, type 2 diabetes, and gestational diabetes), non-alcoholic steatotic liver disease, steatosis of the liver, polycystic ovarian syndrome, hyperlipidemia, and Metabolic Syndrome. The compositions and pharmaceutical combinations may be used for treating obesity or diseases characterized by overeating and for the suppression of appetite. The methods comprise administering to a subject a therapeutically effective amount of a composition of the invention to a subject in need thereof, preferably a human subject.

Other disorders that may be treated with the compositions and combinations of the invention include, but are not limited to, insulin resistance, insulin deficiency, hyperinsulinemia, hyperglycemia, dyslipidemia, hyperlipidemia, hyperketonemia, hyperglucagonemia, pancreatitis, pancreatic neoplasms, cardiovascular disease, hypertension, coronary artery disease, atherosclerosis, renal failure, neuropathy (e.g., autonomic neuropathy, parasympathetic neuropathy, and polyneuropathy), diabetic retinopathy, cataracts, endocrine disorders, and sleep apnea, polycystic ovarian syndrome, neoplasms of the breast, colon, prostate, rectum and ovarian, osteoarthritis steatosis of the liver.

The invention further encompasses methods of regulating insulin responsiveness in a patient, as well as methods of increasing glucose uptake by a cell, and methods of regulating insulin sensitivity of a cell, using the conjugates or fusions of the invention. Also provided are methods of stimulating insulin synthesis and release, enhancing adipose, muscle or liver tissue sensitivity towards insulin uptake, stimulating glucose uptake, slowing digestive process, slowing of gastric emptying, inhibition of gastric acid secretion, inhibition of pancreatic enzyme secretion, reducing appetite, inhibition of food intake, modifying energy expenditure, or blocking the secretion of glucagon in a patient, comprising administering to said patient a composition of the invention e.g. comprising administering at least one dose of a composition e.g. a pharmaceutical composition or pharmaceutical combination of the present invention.

The invention also provides for use of a composition of the invention in the manufacture of a medicament for treatment of a metabolic disease such as those described herein. The invention also relates to use of any of the compositions described herein for use in therapy.

The polypeptides of the present invention and their salts may be employed alone or in combination with other therapeutic agents (a "pharmaceutical combination") for the treatment of the above-mentioned conditions. In some embodiments, the polypeptide of the present invention and the additional therapeutic agent or agents are administered together, while in other embodiments, the polypeptide of the invention and the additional therapeutic agent or agents are administered separately. When administered separately, administration may occur simultaneously or sequentially, in any order. The amounts of the polypeptides(s) of the present invention and the other therapeutic agent(s) and the relative timings of administration will be selected in order to achieve the desired combined therapeutic effect. The administration in combination of a compound of the present invention with other treatment agents may be in combination by administration concomitantly in: (1) a unitary pharmaceutical composition including both therapeutic agents; or (2) separate pharmaceutical compositions each including one of the therapeutic agents. Alternatively, the combination may be administered separately in a sequential manner wherein one treatment agent is administered first and the other second or vice versa. Such sequential administration may be close in time or remote in time.

In one embodiment, the pharmaceutical combinations of the invention include a polypeptide according to the invention and an exendin-4 peptide (see, for example, U.S. Pat. No. 5,424,286) or a fragment or analog thereof. Exendin-4 (Ex-4) and analogs thereof that are useful for the present invention include Byetta® and Bydureon® (exenatide), Victoza® (liraglutide), lixisenatide, LY2189265 (dulaglutide), PF-4856883, ZYD-1, and HM11260C (LAPS exendin) as well as those described in PCT patent publications WO 99/25728 (Beeley et al.), WO 99/25727 (Beeley et al.), WO 98/05351 (Young et al.), WO 99/40788 (Young et al.), WO 99/07404 (Beeley et al.), and WO 99/43708 (Knudsen et al.).

In another embodiment, the pharmaceutical combinations of the invention include a polypeptide according to the invention and GLP-1 (see, for example, Gutniak, M., et al. (1992) *N. Engl. J. Bled.* 326:1316-22), or a fragment or analog thereof, for example, GLP-1(7-37), GLP-1(7-36), GLP-1(7-35), GLP-1(7-38), GLP-1(7-39), GLP-1(7-40), GLP-1(7-41).

Further GLP-1 analogues are described in International Patent Application No. 90/11299, which relates to peptide fragments which comprise GLP-1(7-36) and functional derivatives thereof and have an insulinotropic activity which exceeds the insulinotropic activity of GLP-1(1-36) or GLP-1(1-37) and to their use as insulinotropic agents (incorporated herein by reference, particularly by way of examples of drugs for use in the present invention).

International Patent Application No. WO 91/11457 (Buckley et al.) discloses analogues of the active GLP-1 peptides GLP-1(7-34), GLP-1(7-35), GLP-1(7-36), and GLP-1(7-37) which can also be useful as GLP-1 drugs according to the present invention (incorporated herein by reference, particularly by way of examples of drugs or agents for use in the present invention).

The pharmaceutical combinations of the invention also include a polypeptide according to the invention and albiglutide.

In another embodiment, the pharmaceutical combinations include a polypeptide according to the invention and an enhancer of GLP-1 action such as a DPP-IV inhibitor (e.g. sitagliptin and/or saxagliptin).

In other embodiments, the pharmaceutical combination comprises a PYY analog of the present invention and one or more therapeutic agents that are direct or indirect stimulators of GLP-1 secretion such as metformin, bile acid sequestrants (e.g. colestipol, cholestryramine, and/or colesevelam), ileal bile acid transport (iBAT) Inhibitors (e.g. ALBI-3309, AZD-7806, S-8921, SAR-58304, or those described in US20130029938), and SGLT-1 Inhibitors (e.g. DSP-3235 and/or LX-4211).

The invention provides for methods of treatment where a "therapeutically effective amount" of a polypeptide of the invention is administered to a subject in need of such treatment. The term "therapeutically effective amount" means any amount which, as compared to a corresponding subject who has not received such amount, results in improved treatment, healing or amelioration of a disease, disorder, or side effect, or a decrease in the rate of advancement of a disease or disorder. As will be recognized by those in the field, an effective amount of therapeutic agent will vary with many factors including the age and weight of the patient, the patient's physical condition, the blood sugar level, the weight level to be obtained, and other factors In one embodiment, a therapeutically effective amount of a polypeptide of the present invention is the amount required to suppress appetite in the subject to a desired degree. The effective daily appetite-suppressing dose of the compounds will typically be in the range of about 0.01 µg to about 500 µg/day, preferably about 0.05 µg to about 100 µg/day and more preferably about 1 µg to about 50 µg/day, most preferably about 5 µg to about 25 µg/day, for a 70 kg patient, administered in a single or divided doses.

In one aspect, the invention provides a pharmaceutical composition comprising a polypeptide of the invention, and a pharmaceutically acceptable carrier, excipient or diluent.

The pharmaceutical compositions and pharmaceutical combinations of the invention can be administered by any route, including intravenously, intraperitoneal, subcutaneous, and intramuscular, orally, topically, transmucosally, or by pulmonary inhalation. For example, polypeptides of the invention can be provided in the form of formulations suitable for parenteral (including intravenous, intramuscular and subcutaneous), nasal or oral administration.

Methods for formulating and delivering polypeptides for various routes of administration are known in the art. See, for example, Swain et al. (2013) *Recent Pat. Biotechnol.* 1 Feb. 2013 Epub ahead of print, Hovgaard, Lars, Sven Froklaer, and Marco Van De Weert, eds. *Pharmaceutical Formulation Development of Peptides and Proteins.* $2^{nd}$ ed. Boca Raton: CRC Press, 2012, and Van Der Walle, Chris, ed. *Peptide and Protein Delivery.* London: Academic, 2011.

In one embodiment, the invention encompasses a slow release formulation. Such formulations allow for therapeutically effective amounts of the therapeutic polypeptide or polypeptides to be delivered into the bloodstream over many hours or days following injection or delivery to the subcutaneous space.

Slow release formulations of the invention may include one or more polymers useful in delaying the release of the therapeutic polypeptide. Non-limiting examples of such polymers include poly(lactic-co-glycolic acid) PLGA, polycaprolactone, polydioxanone, polytrimethylene carbonate, polyanhydrides, PEG-PLGA, polyglutamic acid, polyethylene glycol terphthalate/polybutylene terphthalate/polybutylene terphthalate, poly(aminoacid)-Leu/Glu copolymer, polytyrosine carbonates, polyesteramides, poly(alpha aminoacid) based polymeric micelles, polyhydroxypropylmethacrylamide, polyalkylcyanoacrylate, collagen, hyaluronic acide, albumin, carboxymethylcellulose, fleximer, chitosan, maltodextrin, dextran, or dextran sulfate, In one aspect, the polypeptides of the invention may be delivered via a miniature device such as an implantable infusion pump which is designed to provide long-term continuous or intermittent drug infusion. Such devices can be used to administer a therapeutic polypeptide of the invention via intravenous, intra-arterial, subcutaneous, intraperitoneal, intrathecal, epidural, or intraventricular routes. Such devices may be erodible, non-erodible and/or durable. Non-limiting examples of such devices include the Durasert™ device (pSivida), the DUROS® osmotic delivery system (Intarcia Therapeutics), MedLaunch™ Polymer Technology (Endo Health).

Other devices that could be used according to the present invention include the SnychroMed® pump (Medtronic), and the Codman® 3000 infusion pump (Johnson & Johnson), the V-Go® delivery system (Valeritas), the OmniPod® pump (Insulet), and the JewelPump™ (Debiotech).

The polypeptides of the invention may be administered in an in situ gel formulation. Such formulations typically are administered as liquids which form a gel either by dissipation of the water miscible organic solvent or by aggregation of hydrophobic domains present in the matrix. Non-limiting examples include the FLUID CRYSTAL technology (Camurus) and the SABER technology (Durect), and the formulations described in U.S. Pat. Nos. 5,612,051, 5,714,159, 6,413,539, 6,004,573, and 6,117,949.

The therapeutic polypeptides of the invention may also be encapsulated into a microsphere-based pharmaceutical formulation suitable for subcutaneous injection. Non-limiting examples of microsphere-based formulations for the delivery of peptides include Chroniject™ (Oakwood Labs), Medusa® (Flamel's), Q-Sphera (Q-CHIP), as well as those described in U.S. Pat. Nos. 4,675,189, 6,669,961, and Amin et al. (2001) *J of Controlled Release* 73: 49-57.

The formulation may contain antibacterial or antifungal agents such as meta-cresol, benzyl alcohol, parabens (methyl, propyl, butyl), chlorobutanol, phenol, phenylmercuric salts such as acetate, borate, or nitrate, or sorbic acid.

The compositions of this invention can be lyophilized for storage and reconstituted in a suitable carrier prior to use. Any suitable lyophilization method (e.g., spray drying, cake drying) and/or reconstitution techniques can be employed. In a particular embodiment, the invention provides a composition comprising a lyophilized (freeze dried) polypeptide as described herein.

In certain aspects, the invention provides a nucleic acid encoding a polypeptide of the invention and recombinant expression vectors containing such nucleic acids. Recombinant expression vectors of the invention include a nucleic acid encoding a polypeptide of the invention operably linked to one or more expression control elements such as, e.g., a promoter.

Host cells containing a nucleic acid or recombinant expression vector encoding a polypeptide of the invention are also included. Suitable host cells according to the invention include both prokaryotic host cells and eukaryotic hosts cells. Possible host cells include, but are not limited to, mammalian host cells, bacterial host cells (e.g. *E. coli*), yeast host cells, and plant host cells.

Nucleic acids and recombinant expression vectors encoding a polypeptide of the invention can be introduced into a suitable host cell to create a recombinant host cell using any method appropriate to the host cell selected, e.g., transformation, transfection, electroporation, or infection. In some embodiments, the nucleic acid or recombinant expression vector is integrated into the host cell genome. The resulting recombinant host cell can be maintained under conditions suitable for expression (e.g., in the presence of an inducer, in a suitable animal, in suitable culture media supplemented with appropriate salts, growth factors, antibiotics, nutritional supplements, etc.), whereby the encoded polypeptide is produced. If desired, the encoded peptide or polypeptide can be isolated or recovered.

The invention further provides a method for producing a polypeptide of the present invention where the method comprises maintaining a host cell such as those described above that comprises a nucleic acid or recombinant expression vector that encodes a polypeptide of the invention under conditions suitable for expression of said nucleic acid or recombinant expression vector. Methods for recombinant expression of polypeptides in host cells are well known in the art. See, for example, Rosalyn M. Bill, ed. *Recombinant Protein Production in Yeast: Methods and Protocols* (*Methods in Molecular Biology*, Vol. 866), Humana Press 2012; James L. Hartley, ed. *Protein Expression in Mammalian Cells: Methods and Protocols* (*Methods in Molecular Biology*), Humana Press 2012, Löic Faye and Veronique Gomord, eds. *Recombinant Proteins From Plants Methods and Protocols* (*Methods in Molecular Biology*), Humana Press 2008; and Argelia Lorence, ed. *Recombinant Gene Expression* (*Methods in Molecular Biology*), Humana press 2011.

In certain embodiments, the nucleic acids of the invention are "isolated." Nucleic acids referred to herein as "isolated" are nucleic acids which have been separated away from other material (e.g., other nucleic acids such as genomic DNA, cDNA and/or RNA) in its original environment (e.g., in cells or in a mixture of nucleic acids such as a library). An isolated nucleic acid can be isolated as part of a recombinant expression vector.

The following examples are intended for illustration only and are not intended to limit the scope of the invention in any way.

EXAMPLES

The examples make use of the following abbreviations:
amu atomic mass unit
Fmoc 9-fluorenylmethoxycarbonyl
HBTU 2-(1H-benzotriazole-1-yl)-1,1,3,3-tetramethyl uronium hexafluorophosphate
HCTU 2-(6-chloro-1-H-benzotriazole-1-yl)-1,1,3,3-tetramethylaminium hexafluorophosphate
DMF N,N-dimethylformamide
NMM N-methylmorpholine
DIPEA N,N-diisopropylethylamine
TFA trifluoroacetic acid
Trt trityl
t-Bu tert-butyl
Boc tert-butylcarbonyl
Pbf 2,2,4,6,7-pentamethyldihydro-benzofuran-5-sulfonyl MAL maleimide
PBS phosphate buffered saline
ivDde 1-(4,4-dimethyl-2,6-dioxocyclohexylidene)-3-methylbutyl
MALDI matrix assisted laser desorption/ionization
BMPS N-β-maleimidopropyloxysuccinimide ester
DODT 2,2'-(ethylenedioxy)diethanethiol
TIPS triisopropylsilane
MPA mercaptopropionic acid
rt retention time
RPM revolutions per minute Peptide Synthesis The peptides shown in the following examples were synthesized by solid-phase methods using Fmoc strategy with 2-(1H-benzotriazole-1-yl)-1,1,3,3-tetramethyl uronium hexafluorophosphate (HBTU) or 2-(6-chloro-1-H-benzotriazole-1-yl)-1,1,3,3-tetramethylaminium hexafluorophosphate (HCTU) activation (5 fold molar excess) in N,N-dimethylformamide (DMF), and N-methylmorpholine (NMM) as base, 20% piperidine/DMF for Fmoc deprotection, on an automated peptide synthesizer (model Prelude or Overture; Protein Technologies, Tucson, Ariz.). The resin was Rink Amide MBHA LL (Novabiochem) or Rink Amide AM LL (Novabiochem) with a loading of 0.29-0.38 mmol/g on a 20-400 µmol scale. The side chain protection groups used were Trt for Asn, Gln, Cys and His; t-Bu for Ser, Thr, and Tyr; Boc for Lys and Trp; Ot-Bu for Asp and Glu; and Pbf for Arg. Cleavage of peptide-resin was completed with a mixture of trifluoroacetic acid (TFA):anisole:water:triisopropylsilane (88:5:5:2). The crude peptide was precipitated in cold diethyl ether, the diethyl ether was decanted and the solids triturated again with cold diethyl ether. The crude solids were then purified by reverse phase HPLC on a Waters XBridge™ BEH 130, C18, 10 µm, 130 Å, 30×250 mm ID column, using a gradient within the ranges of 5-75% acetonitrile/water with 0.1% TFA over 30-45 minutes at a flow rate of 30 mL/min, λ—215 nm.

LC/MS Conditions

Method A: Performed using a Phenomenex UPLC Aeris™ Peptide XB C18 column, 1.7 µm, 2.1×100 mm or ACQUITY BEH300 or BEH130 C18 column, 1.77 µm, 2.1×100 mm using 5-65% acetonitrile/water with 0.05% TFA over 30 minutes with a flow rate 0.5 mL/min, λ—215 nm, 280 nm.

C18 HPLC Conditions:

Method A: Performed using a Waters XBridge™ BEH130 C18 column, 5 µm, 4.6×250 mm, with 5-70% acetonitrile/water with 0.1% TFA over 15 minutes with a flow rate 1.5 mL/min, 40° C., λ—215 nm, 280 nm.

Method B: Performed using a Waters XBridge™ BEH130 C18 column, 5 µm, 4.6×250 mm, 5-75% acetonitrile/water with 0.1% TFA over 20 minutes with a flow rate 1.5 mL/min, λ—215 nm, 280 nm.

Method C: Performed using a Waters XBridge™ BEH130 C18 column, 5 µm, 4.6×250 mm, 20-37.5% acetonitrile/water with 0.1% TFA over 15 minutes with a flow rate 1.0 mL/min, 60° C., λ—215 nm, 280 nm.

Method D: Performed using a Waters XBridge™ BEH300 C18 column, 5 µm, 4.6×250 mm, 5-70% acetonitrile/water with 0.1% TFA over 15 minutes with a flow rate 1.5 mL/min, λ—215 nm, 280 nm.

Example 1

PKPEAPGKDASPEELNRYYASLRHYLNWVTRQRY-NH$_2$ (SEQ ID NO:3)

Example 1 was prepared on a 35 µmol scale as a white solid using the general method. The molecular mass of the isolated peptide was confirmed by fragment ions (M+3)/3-1369 amu and (M+4)/4-1027 amu, which corresponds to a peptide with the parent molecular weight of 4105 amu (ESI-MS, LC/MS Method A). A purity of >90% was determined by C18 HPLC (C18 HPLC Method A, rt=8.90 min) for the isolated peptide (25 mg, as the 8 trifluoroacetic acid salt).

Example 2

PKPEAPGKDASPEELNRYYASLRKYLNWLTRQRY-NH$_2$ (SEQ ID NO:4)

Example 2 was prepared on a 35 µmol scale as a white solid using the general method. The molecular mass of the isolated peptide was confirmed by fragment ions (M+3)/3-1371 amu and (M+4)/4-1028 amu, which corresponds to a peptide with the parent molecular weight of 4111 amu (ESI-MS, LC/MS Method A). A purity of >90% was determined by C18 HPLC (C18 HPLC Method A, rt=9.46 min) for the isolated peptide (20 mg, as the 8 trifluoroacetic acid salt).

Example 3

PKPEAPGKDASPEELNRYYASLRHYLNWLTRQRY-NH$_2$ (SEQ ID NO:5)

Example 3 was prepared on a 35 µmol scale as a white solid using the general method. The molecular mass of the isolated peptide was confirmed by fragment ions (M+3)/3-1374 amu and (M+4)/4-1031 amu, which corresponds to a peptide with the parent molecular weight of 4120 amu (ESI-MS, LC/MS Method A). A purity of >90% was determined by C18 HPLC (C18 HPLC Method A, rt=9.42 min) for the isolated peptide (16 mg, as the 8 trifluoroacetic acid salt).

Example 4

PKPEAPGKDASPEEWNRYYADLRKYLNWLTRQRY-NH$_2$ (SEQ ID NO:6)

Example 4 was prepared on a 35 µmol scale as a white solid using the general method. The molecular mass of the isolated peptide was confirmed by fragment ions (M+3)/3-1405 amu and (M+4)/4-1054 amu, which corresponds to a peptide with the parent molecular weight of 4212 amu (ESI-MS, LC/MS Method A). A purity of >90% was determined by C18 HPLC (C18 HPLC Method A, rt=9.54 min) for the isolated peptide (18 mg, as the 8 trifluoroacetic acid salt).

Example 5

PKPEAPGKDASPEEWNRYYADLRHYLNWLTRQRY-NH$_2$ (SEQ ID NO:7)

Example 5 was prepared on a 6×50 µmol scale as a white solid using the general method. The molecular mass of the isolated peptide was confirmed by fragment ions (M+3)/3-1407 amu and (M+4)/4-1056 amu, which corresponds to a peptide with the parent molecular weight of 4221 amu (ESI-MS, LC/MS Method A). A purity of >90% was determined by C18 HPLC (C18 HPLC Method A, rt=9.27 min) for the isolated peptide (180 mg, as the 8 trifluoroacetic acid salt).

Alternatively, Example 5 was prepared via manual synthesis using a 250 mL jacketed reactor that was cooled to 15° C. Rink Amide AM Resin LL (100-200 mesh, 13.8 g, 0.29 mmol/g loading) was swelled with DMF (50 mL) 3 times for 10 min each with nitrogen sparge. The Fmoc group was removed with 20% piperidine in DMF (200 mL) over 5 min with nitrogen sparge, followed by 20% piperidine in DMF (200 mL) over 12 min with nitrogen sparge. The resin was then washed with DMF (100 mL) and then twice with DMF (100 mL) for 1 min with nitrogen sparge. Following Fmoc deprotecion and DMF washing, the first amino acid (100 mL, 200 mM solution in DMF) was added, followed by DIPEA solution (50 mL, 800 mM solution in DMF). A solution of HCTU in DMF (50 mL, 400 mM) was added over a 12 min period via peristaltic pump. After a minimum of 15 min, a Kaiser test on an aliquot of resin was performed to ensure complete reaction. The resin was then washed with DMF (100 mL) and then twice with DMF (100 mL) for 1 min with nitrogen sparge. This sequence (Fmoc deprotection with 20% piperidine/DMF; washes; amino acid coupling; Kaiser test; washes) was performed for the remaining sequence of the peptide, except for the histidine at position 24. The amino acid (His) and DIPEA solutions were cooled to -10° C. and added to the reactor. The reactor's chiller was set to 5° C. and the reaction mixture cooled to 6.3° C. in ~15 min. A cooled (~10° C.) solution of HCTU in DMF (50 mL) was added dropwise over a 25 min period via peristaltic pump at 2 mL/min, during which time the solution warmed to 7.8° C. After 15 min, a Kaiser test showed complete reaction. The remaining amino acids were coupled using the standard protocol. At the completion of the synthesis (proline 1 was coupled), the resin was then washed twice with DMF (100 mL) for 1 min with nitrogen sparge, then washed three time with DCM (200 mL) for 5 min with nitrogen sparge, and then finally three times with methanol (200 mL) for 5 min with nitrogen sparge. The resin was dried with nitrogen sparge for 30 min to give 37.5 g of dry resin. The resin was cleaved in portions. Ten grams of resin was swelled with 120 mL DMF for 45 min with nitrogen sparge. The DMF was drained off and the final N-terminal Fmoc was removed with 20% piperidine in DMF (150 mL) over 5 min with nitrogen sparge, followed by 20% piperidine in DMF (150 mL) over 12 min with nitrogen sparge. The resin was then washed with DMF (100 mL) and then twice with DMF (100 mL) for 1 min with nitrogen sparge, then washed three time with DCM (120 mL) for 5 min with nitrogen sparge, and then finally three times with methanol (120 mL) for 5 min with nitrogen sparge. The resin was dried with nitrogen sparge for 30 min. Cleavage of peptide from the resin was performed using 100-120 mL of cleavage cocktail: TFA:phenol:DODT:water:TIPS (90:2.5:2.5:2.5:2.5) for 2.5-3 h. The filtrates were split into vessels and treated with cold diethyl ether. The vessels were centrifuged for 10 min at 3000 RPM and the supernatant was poured off. The material was treated with cold diethyl ether again, shaken and then centrifuged for another 10 min at 3000 RPM. The supernatant was poured off again. The solids from the vessels were combined using 0.1% aqueous TFA and lyophilized to give batch 1. The resin was subjected to second cleavage using the same procedure to give batch 2. This process (Fmoc deprotection; washes; cleavage from resin, trituration/resuspension, and lyophilization) was repeated three times with ~9 g of resin to afford a total of ~11 g of crude peptide after lyophilization. This material was dissolved in 0.1% aqueous TFA to give an approximate concentration of 75 mg/mL and the material was purified by reverse phase HPLC using multiple injections (between 2 and 3 mL each) using the following step gradient: 5-41.25% acetonitrile/water with 0.1% TFA over 75 min; XBridge™ Prep C18, 50×250 mm, 10 µm, flow rate 50 mL/min. Fractions containing product with >93% purity (HPLC Method C) were combined. Impure fractions (purity of ~88-93%) were also collected and resubjected to the purification conditions. All pure fractions (>93%) were then combined and freeze-dried to give desired peptide as a white solid. A purity of >93% was determined by C18 HPLC (C18 HPLC Method C, rt=14.12 min) for the isolated peptide (2.8 g, as the 8 trifluoroacetic acid salt).

A salt exchange from TFA to HOAc using Example 5 prepared by peptide synthesizer and manual synthesis was performed using a 2×60 mL Agilent StratoSpheres™ PL-HCO$_3$ MP SPE column. The column was equilibrated by first treating with 50 mL of MeOH, followed by 50 mL of DI water. The column was then treated with 2×50 mL 1 N HOAc and then with 2×50 mL 0.1 N HOAc, and the filtrate was monitored to ensure pH ~3 (pH paper). A solution of Example 5 (~3.5 g including 2.8 g prepared as described above and 0.7 g derived from previously-prepared batches) in 0.1 N HOAc was split equally between the SPE columns and then eluted with 5×50 mL of 0.1 N HOAc. The column was then washed with 5×50 mL of MeOH. The methanol fractions containing product (as determined by HPLC, Method C) were concentrated via rotary evaporator to ~40 mL, which was added to the 0.1 N HOAc washes. The solution was freeze-dried over 3 d to afford the desired isolated peptide as a white solid. A purity of >95% was determined by C18 HPLC (C18 HPLC Method C, rt=14.14 min) for the isolated peptide (2.95 g, as the 8 acetic acid salt).

Example 6

PKPEAPGKDASPEEWNRYYASLRKYLNW-
LTRQRY-NH$_2$ (SEQ ID NO:8)

Example 6 was prepared on a 35 µmol scale as a white solid using the general method. The molecular mass of the isolated peptide was confirmed by fragment ions (M+3)/3-1395 amu and (M+4)/4-1047 amu, which corresponds to a peptide with the parent molecular weight of 4184 amu (ESI-MS, LC/MS Method A). A purity of >90% was determined by C18 HPLC (C18 HPLC Method A, rt=9.45 min) for the isolated peptide (18 mg, as the 8 trifluoroacetic acid salt).

Example 7

PKPEAPGKDASPEEWNRYYASLRHYLNWL-
TRQRY-NH$_2$ (SEQ ID NO:9)

Example 7 was prepared on a 35 µmol scale as a white solid using the general method. The molecular mass of the isolated peptide was confirmed by fragment ions (M+3)/3-1398 amu and (M+4)/4-1049 amu, which corresponds to a peptide with the parent molecular weight of 4193 amu (ESI-MS, LC/MS Method A). A purity of >90% was determined by C18 HPLC (C18 HPLC Method A, rt=9.47 min) for the isolated peptide (27 mg, as the 8 trifluoroacetic acid salt).

Example 8

PKPEAPGKDASPEEWNRYYADLRKYLN-
WVTRQRY-NH$_2$ (SEQ ID NO:10)

Example 8 was prepared on a 35 µmol scale as a white solid using the general method. The molecular mass of the isolated peptide was confirmed by fragment ions (M+3)/3-1400 amu and (M+4)/4-1050 amu, which corresponds to a peptide with the parent molecular weight of 4198 amu (ESI-MS, LC/MS Method A). A purity of >90% was determined by C18 HPLC (C18 HPLC Method A, rt=9.35 min) for the isolated peptide (21 mg, as the 8 trifluoroacetic acid salt).

Example 9

PKPEAPGKDASPEEWNRYYADLRHYLNW-VTRQRY-NH$_2$ (SEQ ID NO:11)

Example 9 was prepared on a 35 μmol scale as a white solid using the general method. The molecular mass of the isolated peptide was confirmed by fragment ions (M+3)/3-1403 amu and (M+4)/4-1052 amu, which corresponds to a peptide with the parent molecular weight of 4207 amu (ESI-MS, LC/MS Method A). A purity of >90% was determined by C18 HPLC (C18 HPLC Method A, rt=9.36 min) for the isolated peptide (22 mg, as the 8 trifluoroacetic acid salt).

Example 10

PKPEAPGKDASPEEWNRYYASLRKYLNWV-TRQRY-NH$_2$ (SEQ ID NO:12)

Example 10 was prepared on a 35 μmol scale as a white solid using the general method. The molecular mass of the isolated peptide was confirmed by fragment ions (M+3)/3-1391 amu and (M+4)/4-1043 amu, which corresponds to a peptide with the parent molecular weight of 4170 amu (ESI-MS, LC/MS Method A). A purity of >90% was determined by C18 HPLC (C18 HPLC Method A, rt=9.23 min) for the isolated peptide (23 mg, as the 8 trifluoroacetic acid salt).

Example 11

PKPEAPGKDASPEEWNRYYASLRHYLN-WVTRQRY-NH$_2$ (SEQ ID NO:13)

Example 11 was prepared on a 35 μmol scale as a white solid using the general method. The molecular mass of the isolated peptide was confirmed by fragment ions (M+3)/3-1393 amu and (M+4)/4-1045 amu, which corresponds to a peptide with the parent molecular weight of 4179 amu (ESI-MS, LC/MS Method A). A purity of >90% was determined by C18 HPLC (C18 HPLC Method A, rt=9.24 min) for the isolated peptide (22 mg, as the 8 trifluoroacetic acid salt).

Example 12

PKPEAPGEDASPEELNRYYASLRHYLNWVT-RQRY-NH$_2$ (SEQ ID NO:14)

Example 12 was prepared on a 35 μmol scale as a white solid using the general method. The molecular mass of the isolated peptide was confirmed by fragment ions (M+3)/3-1369 amu and (M+4)/4-1027 amu, which corresponds to a peptide with the parent molecular weight of 4106 amu (ESI-MS, LC/MS Method A). A purity of >90% was determined by C18 HPLC (C18 HPLC Method A, rt=9.60 min) for the isolated peptide (22 mg, as the 7 trifluoroacetic acid salt).

Example 13

PKPEHPGKDASPEEWNRYYAALRKYLNW-VTRQRY-NH$_2$ (SEQ ID NO:15)

Example 13 was prepared on a 35 μmol scale as a white solid using the general method. The molecular mass of the isolated peptide was confirmed by fragment ions (M+3)/3-1407 amu and (M+4)/4-1056 amu, which corresponds to a peptide with the parent molecular weight of 4220 amu (ESI-MS, LC/MS Method A). A purity of >90% was determined by C18 HPLC (C18 HPLC Method A, rt=9.46 min) for the isolated peptide (22 mg, as the 9 trifluoroacetic acid salt).

Example 14

PKPEHPGKDASPEELNKYYAALRHYLN-WVTRQRY-NH$_2$ (SEQ ID NO:16)

Example 14 was prepared on a 35 μmol scale as a white solid using the general method. The molecular mass of the isolated peptide was confirmed by fragment ions (M+3)/3-1377 amu and (M+4)/4-1033 amu, which corresponds to a peptide with the parent molecular weight of 4128 amu (ESI-MS, LC/MS Method A). A purity of >90% was determined by C18 HPLC (C18 HPLC Method A, rt=8.88 min) for the isolated peptide (27 mg, as the 9 trifluoroacetic acid salt).

Example 15

PKPEHPGKDASPEELNRYYASLRHYIN-WVTRQRY-NH$_2$ (SEQ ID NO:17)

Example 15 was prepared on a 35 μmol scale as a white solid using the general method. The molecular mass of the isolated peptide was confirmed by fragment ions (M+3)/3-1391 amu and (M+4)/4-1044 amu, which corresponds to a peptide with the parent molecular weight of 4172 amu (ESI-MS, LC/MS Method A). A purity of >90% was determined by C18 HPLC (C18 HPLC Method A, rt=8.77 min) for the isolated peptide (29 mg, as the 9 trifluoroacetic acid salt).

Example 16

PKPEHPGKDASPEELARYYASLRHYL-NWVTRQRY-NH$_2$ (SEQ ID NO:18)

Example 16 was prepared on a 35 μmol scale as a white solid using the general method. The molecular mass of the isolated peptide was confirmed by fragment ions (M+3)/3-1377 amu and (M+4)/4-1033 amu, which corresponds to a peptide with the parent molecular weight of 4129 amu (ESI-MS, LC/MS Method A). A purity of >90% was determined by C18 HPLC (C18 HPLC Method A, rt=8.89 min) for the isolated peptide (30 mg, as the 9 trifluoroacetic acid salt).

Example 17

PKPEHPGKDASPEEWNRYYASLRHYIN-WVTRQRY-NH$_2$ (SEQ ID NO:19)

Example 17 was prepared on a 35 μmol scale as a white solid using the general method. The isolated crude solid was stirred for several hours in 8 mL of 25% acetic acid to minimize the tryptophan $CO_2$ adduct formed during cleavage from the resin. The molecular mass of the isolated peptide was confirmed by fragment ions (M+3)/3-1416 amu and (M+4)/4-1062 amu, which corresponds to a peptide with the parent molecular weight of 4245 amu (ESI-MS, LC/MS Method A). A purity of >90% was determined by C18 HPLC (C18 HPLC Method A, rt=8.88 min) for the isolated peptide (35 mg, as the 9 trifluoroacetic acid salt).

Example 18

PKPEHPGKDASPEEWNRYYADLRHYIN-WVTRQRY-NH$_2$ (SEQ ID NO:20)

Example 18 was prepared on a 35 μmol scale as a white solid using the general method. The isolated crude solid was stirred for several hours in 8 mL of 25% acetic acid to minimize the tryptophan $CO_2$ adduct formed during cleavage from the resin. The molecular mass of the isolated peptide was confirmed by fragment ions (M+3)/3-1425 amu and (M+4)/4-1069 amu, which corresponds to a peptide with the parent molecular weight of 4273 amu (ESI-MS, LC/MS Method A). A purity of >90% was determined by C18 HPLC (C18 HPLC Method A, rt=8.98 min) for the isolated peptide (17 mg, as the 9 trifluoroacetic acid salt).

Example 19

PKPEHPGKDASPEEWNRYYADLRHYLN-WVTRQRY-NH$_2$ (SEQ ID NO:21)

Example 19 was prepared on a 35 μmol scale as a white solid using the general method. The isolated crude solid was stirred for several hours in 8 mL of 25% acetic acid to minimize the tryptophan $CO_2$ adduct formed during cleavage from the resin. The molecular mass of the isolated peptide was confirmed by fragment ions (M+3)/3-1425 amu and (M+4)/4-1069 amu, which corresponds to a peptide with the parent molecular weight of 4273 amu (ESI-MS, LC/MS Method A). A purity of >90% was determined by C18 HPLC (C18 HPLC Method A, rt=8.98 min) for the isolated peptide (34 mg, as the 9 trifluoroacetic acid salt).

Example 20

PKPESPGKDASPEEWNRYYADLRHYIN-WVTRQRY-NH$_2$ (SEQ ID NO:22)

Example 20 was prepared on a 35 μmol scale as a white solid using the general method. The molecular mass of the isolated peptide was confirmed by fragment ions (M+3)/3-1408 amu and (M+4)/4-1057 amu, which corresponds to a peptide with the parent molecular weight of 4223 amu (ESI-MS, LC/MS Method A). A purity of >90% was determined by C18 HPLC (C18 HPLC Method A, rt=8.30 min) for the isolated peptide (28 mg, as the 8 trifluoroacetic acid salt).

Example 21

PKPESPGKDASPEEWNRYYADLRHYLN-WVTRQRY-NH$_2$ (SEQ ID NO:23)

Example 21 was prepared on a 35 μmol scale as a white solid using the general method. The molecular mass of the isolated peptide was confirmed by fragment ions (M+3)/3-1408 amu and (M+4)/4-1057 amu, which corresponds to a peptide with the parent molecular weight of 4223 amu (ESI-MS, LC/MS Method A). A purity of >90% was determined by C18 HPLC (C18 HPLC Method A, rt=8.68 min) for the isolated peptide (28 mg, as the 8 trifluoroacetic acid salt).

Example 22

PKPEHPGKDASPEEWNRYYADLRHYLN-WLTRQRY-NH$_2$ (SEQ ID NO:24)

Example 22 was prepared on a 40 μmol scale as a white solid using the general method. The isolated crude solid was stirred for several hours in 8 mL of 25% acetic acid to minimize the tryptophan $CO_2$ adduct formed during cleavage from the resin. The molecular mass of the isolated peptide was confirmed by fragment ions (M+3)/3-1430 amu and (M+4)/4-1073 amu, which corresponds to a peptide with the parent molecular weight of 4287 amu (ESI-MS, LC/MS Method A). A purity of >90% was determined by C18 HPLC (C18 HPLC Method A, rt=9.65 min) for the isolated peptide (24 mg, as the 9 trifluoroacetic acid salt).

Example 23

PKPEHPGKDASPEEWAKYYAALRHY-INWVTRQRY-NH$_2$ (SEQ ID NO:25)

Example 23 was prepared on a 40 μmol scale as a white solid using the general method. The isolated crude solid was stirred for several hours in 8 mL of 25% acetic acid to minimize the tryptophan $CO_2$ adduct formed during cleavage from the resin. The molecular mass of the isolated peptide was confirmed by fragment ions (M+3)/3-1386 amu and (M+4)/4-1040 amu, which corresponds to a peptide with the parent molecular weight of 4158 amu (ESI-MS, LC/MS Method A). A purity of >90% was determined by C18 HPLC (C18 HPLC Method A, rt=9.28 min) for the isolated peptide (20 mg, as the 9 trifluoroacetic acid salt).

Example 24

PKPEAPGKDASPEEWNRYYADLRHYI-NWVTRQRY-NH$_2$ (SEQ ID NO:26)

Example 24 was prepared on a 40 μmol scale as a white solid using the general method. The isolated crude solid was stirred for several hours in 8 mL of 25% acetic acid to minimize the tryptophan $CO_2$ adduct formed during cleavage from the resin. The molecular mass of the isolated peptide was confirmed by fragment ions (M+3)/3-1403 amu and (M+4)/4-1053 amu, which corresponds to a peptide with the parent molecular weight of 4207 amu (ESI-MS, LC/MS Method A). A purity of >90% was determined by C18 HPLC (C18 HPLC Method A, rt=9.22 min) for the isolated peptide (28 mg, as the 8 trifluoroacetic acid salt).

Example 25

PKPEHPGKDASPEEWNRYYASLRKYL-NWVTRQRY-NH$_2$ (SEQ ID NO:27)

Example 25 was prepared on a 40 μmol scale as a white solid using the general method. The isolated crude solid was stirred for several hours in 8 mL of 25% acetic acid to minimize the tryptophan $CO_2$ adduct formed during cleavage from the resin. The molecular mass of the isolated peptide was confirmed by fragment ions (M+3)/3-1412 amu and (M+4)/4-1060 amu, which corresponds to a peptide with the parent molecular weight of 4236 amu (ESI-MS, LC/MS Method A). A purity of >90% was determined by C18 HPLC (C18 HPLC Method A, rt=9.09 min) for the isolated peptide (21 mg, as the 9 trifluoroacetic acid salt).

Example 26

PKPEHPGKDASAEEWAKYYAALRHYINW-VTRQRY-NH$_2$ (SEQ ID NO:28)

Example 26 was prepared on a 20 µmol scale as a white solid using the general method. The molecular mass of the isolated peptide was confirmed by fragment ions (M+3)/3-1378 amu and (M+4)/4-1034 amu, which corresponds to a peptide with the parent molecular weight of 4132 amu (ESI-MS, LC/MS Method A). A purity of >90% was determined by C18 HPLC (C18 HPLC Method A, rt=9.44 min) for the isolated peptide (19 mg, as the 9 trifluoroacetic acid salt).

Example 27

PKPEAPGKDASAEEWNRYYASLRHYLN-WVTRQRY-NH$_2$ (SEQ ID NO:29)

Example 27 was prepared on a 20 µmol scale as a white solid using the general method. The molecular mass of the isolated peptide was confirmed by fragment ions (M+3)/3-1385 amu and (M+4)/4-1039 amu, which corresponds to a peptide with the parent molecular weight of 4153 amu (ESI-MS, LC/MS Method A). A purity of >90% was determined by C18 HPLC (C18 HPLC Method A, rt=9.31 min) for the isolated peptide (16 mg, as the 8 trifluoroacetic acid salt).

Example 28

PKPEHPGKDASAEELARYYASLRHYL-NWVTRQRY-NH$_2$ (SEQ ID NO:30)

Example 28 was prepared on a 20 µmol scale as a white solid using the general method. The molecular mass of the isolated peptide was confirmed by fragment ions (M+3)/3-1368 amu and (M+4)/4-1027 amu, which corresponds to a peptide with the parent molecular weight of 4103 amu (ESI-MS, LC/MS Method A). A purity of >90% was determined by C18 HPLC (C18 HPLC Method A, rt=9.27 min) for the isolated peptide (14 mg, as the 9 trifluoroacetic acid salt).

Example 29

PKPEAPGKDASAEEWNRYYASLRKYL-NWVTRQRY-NH$_2$ (SEQ ID NO:31)

Example 29 was prepared on a 20 µmol scale as a white solid using the general method. The molecular mass of the isolated peptide was confirmed by fragment ions (M+3)/3-1382 amu and (M+4)/4-1037 amu, which corresponds to a peptide with the parent molecular weight of 4144 amu (ESI-MS, LC/MS Method A). A purity of >90% was determined by C18 HPLC (C18 HPLC Method A, rt=9.31 min) for the isolated peptide (27 mg, as the 8 trifluoroacetic acid salt).

Example 30

PKPESPGKDASAEEWTKYYAALRHYIN-WVTRQRY-NH$_2$ (SEQ ID NO:32)

Example 30 was prepared on a 20 µmol scale as a white solid using the general method. The molecular mass of the isolated peptide was confirmed by fragment ions (M+3)/3-1371 amu and (M+4)/4-1029 amu, which corresponds to a peptide with the parent molecular weight of 4112 amu (ESI-MS, LC/MS Method A). A purity of >90% was determined by C18 HPLC (C18 HPLC Method A, rt=9.59 min) for the isolated peptide (33 mg, as the 8 trifluoroacetic acid salt).

Example 31

PKPEAPGKDASPEELNRYYASLRKYLN-WVTRQRY-NH$_2$ (SEQ ID NO:33)

Example 31 was prepared on a 35 µmol scale as a white solid using the general method. The isolated crude solid was stirred for several hours in 8 mL of 25% acetic acid to minimize the tryptophan CO$_2$ adduct formed during cleavage from the resin. The molecular mass of the isolated peptide was confirmed by fragment ions (M+3)/3-1366 amu and (M+4)/4-1025 amu, which corresponds to a peptide with the parent molecular weight of 4097 amu (ESI-MS, LC/MS Method A). A purity of >90% was determined by C18 HPLC (C18 HPLC Method A, rt=8.93 min) for the isolated peptide (21 mg, as the 8 trifluoroacetic acid salt).

Example 32

PKPEHPGEDASPEEWAKYYAALRH-YINWVTRQRY-NH$_2$ (SEQ ID NO:34)

Example 32 was prepared on a 20 µmol scale as a white solid using the general method. The molecular mass of the isolated peptide was confirmed by fragment ions (M+3)/3-1387 amu and (M+4)/4-1041 amu, which corresponds to a peptide with the parent molecular weight of 4159 amu (ESI-MS, LC/MS Method A). A purity of >90% was determined by LC/MS (LC/MS Method A, rt=13.58 min) for the isolated peptide (9.4 mg, as the 8 trifluoroacetic acid salt).

Example 33

PKPEAPGEDASAEEWNRYYASLRHY-LNWVTRQRY-NH$_2$ (SEQ ID NO:35)

Example 33 was prepared on a 20 µmol scale as a white solid using the general method. The molecular mass of the isolated peptide was confirmed by fragment ions (M+3)/3-1385 amu and (M+4)/4-1039 amu, which corresponds to a peptide with the parent molecular weight of 4154 amu (ESI-MS, LC/MS Method A). A purity of >90% was determined by LC/MS (LC/MS Method A, rt=13.35 min) for the isolated peptide (7.7 mg, as the 7 trifluoroacetic acid salt).

Example 34

PKPESPGEDASPEEWTKYYAALRHYIN-WVTRQRY-NH$_2$ (SEQ ID NO:36)

Example 34 was prepared on a 20 µmol scale as a white solid using the general method. The molecular mass of the isolated peptide was confirmed by fragment ions (M+3)/3-1381 amu and (M+4)/4-1036 amu, which corresponds to a peptide with the parent molecular weight of 4139 amu (ESI-MS, LC/MS Method A). A purity of >90% was determined by LC/MS (LC/MS Method A, rt=13.98 min) for the isolated peptide (8.2 mg, as the 7 trifluoroacetic acid salt).

Example 35

PKPEAPGEDASPEEWNRYYADLRHYLN-WLTRQRY-NH₂ (SEQ ID NO:37)

Example 35 was prepared on a 20 μmol scale as a white solid using the general method. The molecular mass of the isolated peptide was confirmed by fragment ions (M+3)/3-1408 amu and (M+4)/4-1056 amu, which corresponds to a peptide with the parent molecular weight of 4222 amu (ESI-MS, LC/MS Method A). A purity of >90% was determined by LC/MS (LC/MS Method A, rt=13.84 min) for the isolated peptide (7.5 mg, as the 7 trifluoroacetic acid salt).

Examples 36-43 make reference to the following intermediates:

Intermediate 1

(SEQ ID NO: 39)

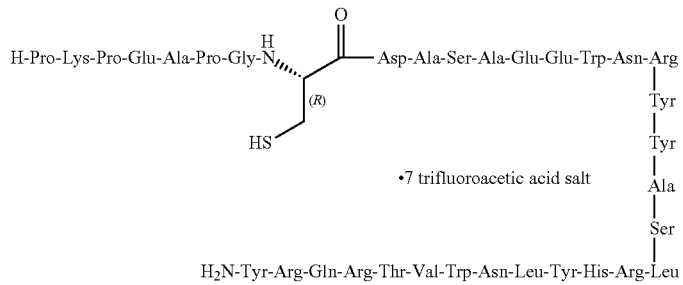

•7 trifluoroacetic acid salt

Intermediate 2

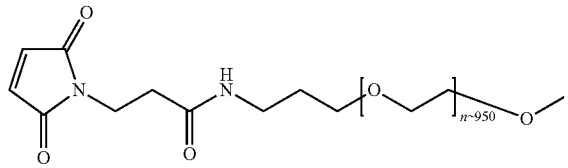

α-[3-(3-maleimido-1-oxopropyl)amino]propyl-ω-methoxy, polyoxethylene
(available from NOF Corporation or JenKEM Technology USA Inc.)

Intermediate 3

(SEQ ID NO: 40)

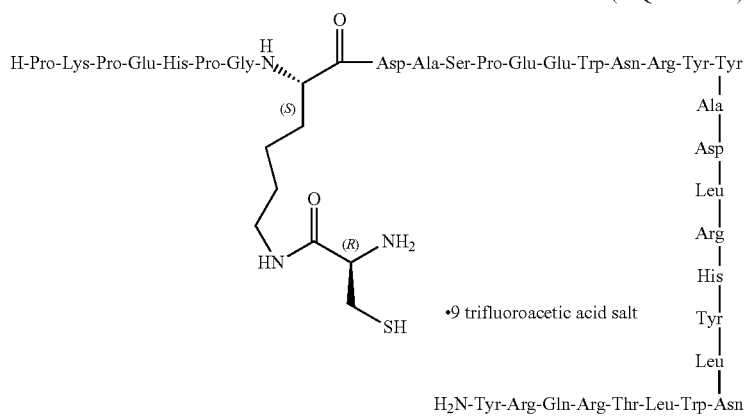

•9 trifluoroacetic acid salt

Intermediate 4

(SEQ ID NO: 41)

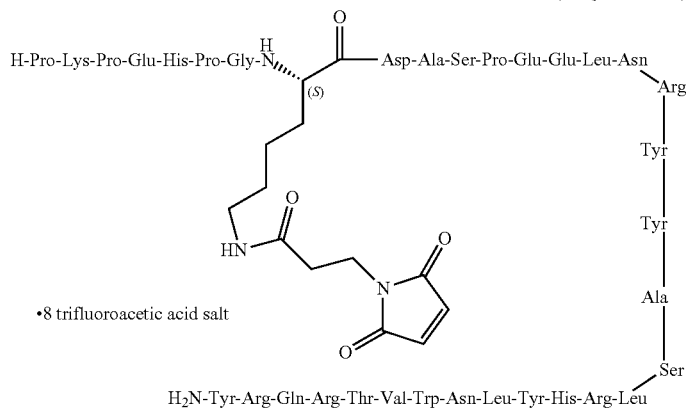

•8 trifluoroacetic acid salt

-continued
Intermediate 5
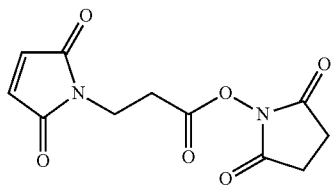
N-succinimidyl-3-maleinimidopropionate
Intermediate 6
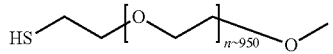
M-SH-40K, available from
JenKem Technology USA Inc.
Intermediate 7
(SEQ ID NO: 42)
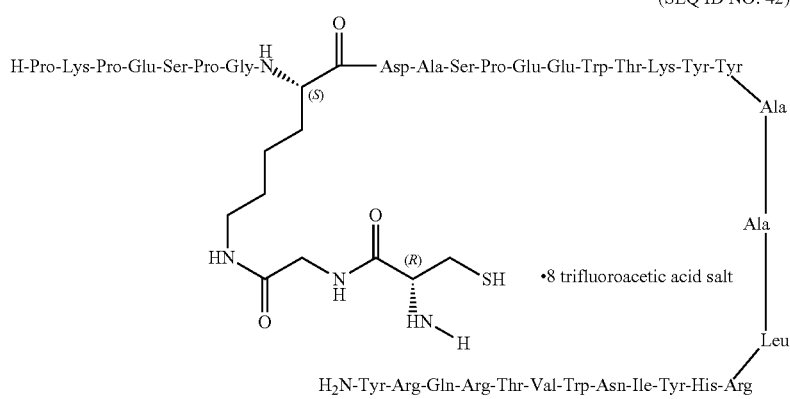
•8 trifluoroacetic acid salt
Intermediate 8
(SEQ ID NO: 43)
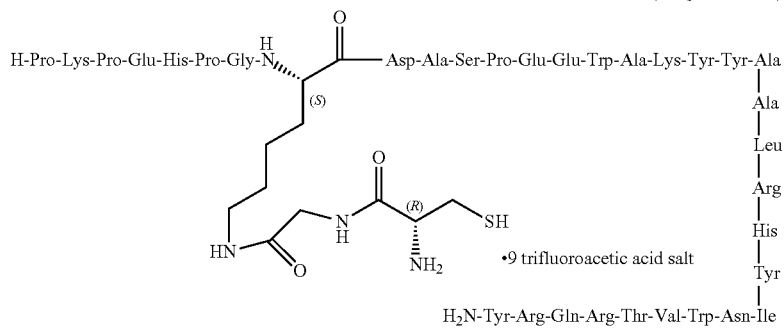
•9 trifluoroacetic acid salt
Intermediate 9
(SEQ ID NO: 44)
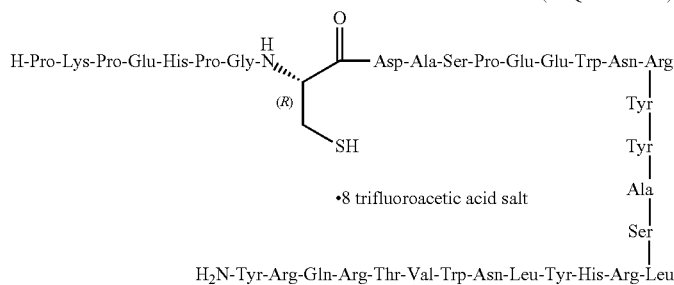
•8 trifluoroacetic acid salt -continued (SEQ ID NO: 43)

Intermediate 10

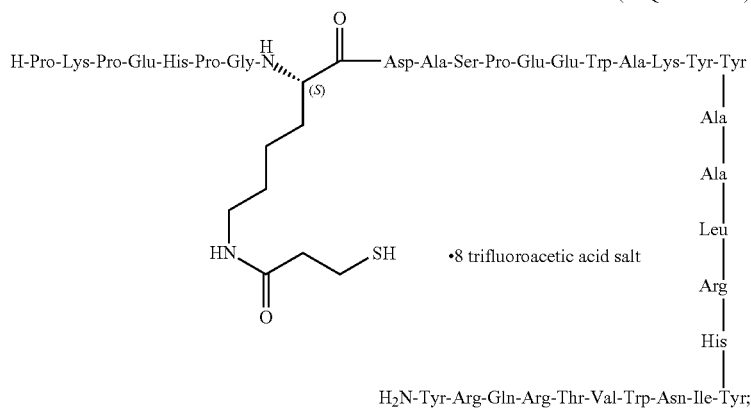

(SEQ ID NO: 45)

Intermediate 11

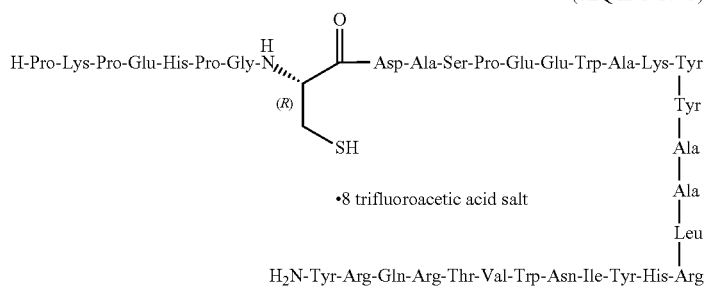

Example 36

(SEQ ID NO: 39)

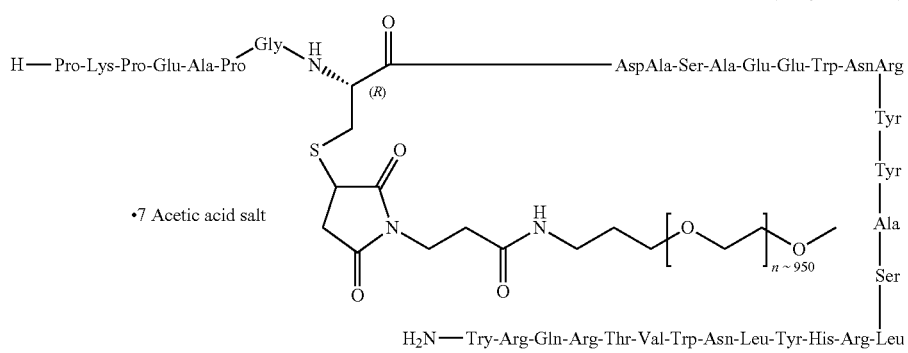

Intermediate 1 was prepared on a 400 µmol scale as a white solid using the general method. The molecular mass of the isolated peptide was confirmed by fragment ions (M+3)/3-1377 amu and (M+4)/4-1033 amu, which corresponds to a peptide with the parent molecular weight of 4128 amu (ESI-MS, LC/MS Method A). A purity of >90% was determined by C18 HPLC (C18 HPLC Method B, rt=10.98 min) for the isolated peptide (76 mg, as the 7 trifluoroacetic acid salt).

A mixture of Intermediate 1 (24.1 mg, 4.89 µmol) and Intermediate 2 (NOF Corporation, ME-400MA, 226 mg, 5.14 µmol) in 3.5 mL of 1×PBS buffer at pH 7.4 was shaken for 45 minutes, during which time the reaction became homogenous. The reaction was then diluted with a solution of 20% MeOH in 0.1 M aqueous HCl and purified by ion exchange chromatography (Sepharose FF Media, 5-50% 1 M NaCl in 20% methanol/10 mM aqueous HCl and over 5 column volumes, flow rate 5 mL/min, λ—254 nm). The purified conjugate was desalted using size exclusion chromatography (GE HiPrep 26/10 Desalting column, 0.1 M acetic acid-, λ—254 nm) to afford a white solid after lyophilization. The molecular mass of the isolated peptide was confirmed by positive fragment ion distribution with the apex at 47379 amu (MALDI). Example 36 (107 mg, as the 7 acetic acid salt) gave a retention time equal to 9.95 min using size exclusion HPLC (Phenomenex BioSep-SEC-53000 column, 7.8×300 mm, 5 µm, 50% acetonitrile/water with 0.5% TFA over 20 min, flow rate 0.75 mL/min, λ—220 nm).

Example 37

(SEQ ID NO: 40)

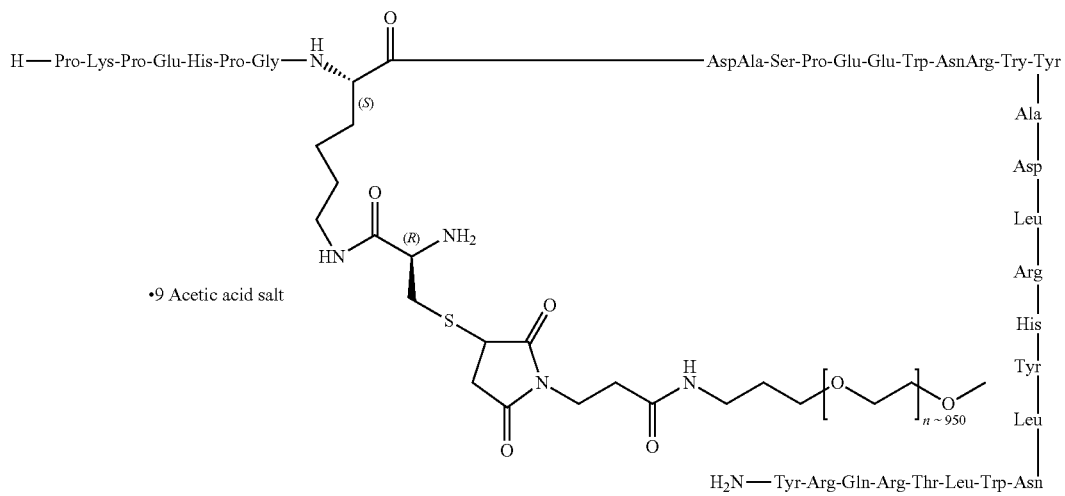

Intermediate 3 was prepared on a 40 μmol scale as a white solid using the general method, except the lysine at position 8 of the peptide was protected with an ivDde group, and proline at position 1 was protected with a Boc. After the coupling of the last amino acid (proline 1), the ivDde was removed with repeated treatments of 4% hydrazine in DMF, and Fmoc-Cys(Trt)-OH was coupled. The molecular mass of the isolated peptide was confirmed by fragment ions (M+3)/3-1464 amu and (M+4)/4-1098 amu, which corresponds to a peptide with the parent molecular weight of 4390 amu (ESI-MS, LC/MS Method A). A purity of >90% was determined by C18 HPLC (C18 HPLC Method D, rt=9.61 min) for the isolated peptide (32 mg, as the 9 trifluoroacetic acid salt).

A mixture of Intermediate 3 (10 mg, 1.85 μmol) and Intermediate 2 (JenKem Technology USA Inc., 74 mg, 1.85 μmol) in 5 mL of 1×PBS buffer at pH 7.4 was shaken overnight, during which time the reaction became homogenous. The reaction was then diluted with 5 mL of 20% MeOH in 10 mM aqueous HCl and purified by ion exchange chromatography (Sepharose FF Media, 0-60% 1 M NaCl in 20% methanol/10 mM aqueous HCl over 7 column volumes, flow rate 5 mL/min, λ—254 nm). The purified conjugate was desalted using size exclusion chromatography (Sephadex G 25 Fine Desalting column, 0.1 M acetic acid, λ—254 nm) to afford a white solid after lyophilization. The molecular mass of the isolated peptide was confirmed by positive fragment ion distribution with the apex at 44568 amu (MALDI). Example 37 (35 mg, as the 9 acetic acid salt) gave a retention time equal to 11.58 min using size exclusion HPLC (Phenomenex BioSep-SEC-53000 column, 7.8×300 mm, 5 μm, 0.15 mM NaCl in 30 mM PBS over 20 min, pH 6.8, flow rate 0.75 mL/min, λ—215 nm).

Example 38

(SEQ ID NO:41)

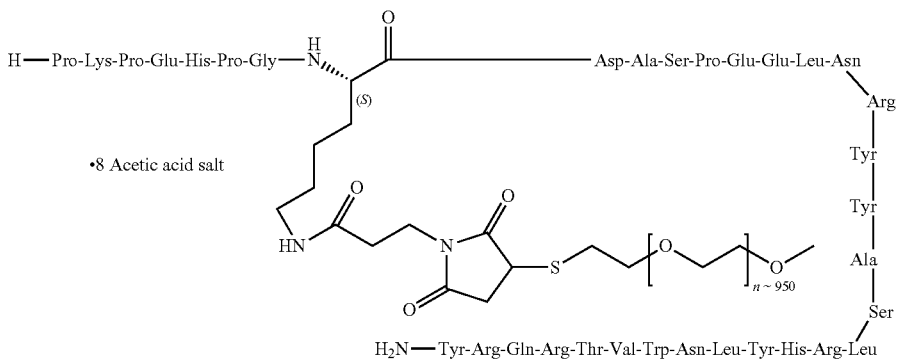

Intermediate 4 was prepared on a 40 μmol scale as a white solid using the general method, except the lysine at position 8 of the peptide was protected with an ivDde group, and proline at position 1 was protected with a Boc. After the coupling of the last amino acid (proline 1), the ivDde was removed with repeated treatments of 4% hydrazine in DMF, and the linker was coupled using the activated succinimide ester reagent Intermediate 5, N-β-maleimidopropyloxysuccinimide ester, without the use of activator (HCTU) or base (NMM). The molecular mass of the isolated peptide was confirmed by fragment ions (M+3)/3-1442 amu and (M+4)/4-1082 amu, which corresponds to a peptide with the parent molecular weight of 4323 amu (ESI-MS, LC/MS Method A). A purity of >90% was determined by C18 HPLC (C18 HPLC Method A, rt=8.79 min) for the isolated peptide (29 mg, as the 8 trifluoroacetic acid salt).

A mixture of Intermediate 4 (10 mg, 1.91 μmol) and Intermediate 6 (JenKem Technology USA Inc., 76 mg, 1.91 μmol) in 5 mL of 1×PBS buffer at pH 7.4 was stirred overnight, during which time the reaction became homogenous. The reaction was then diluted with 5 mL of 20% MeOH in 10 mM aqueous HCl and purified by ion exchange chromatography (Sepharose FF Media, 0-60% 1 M NaCl in 20% methanol/10 mM aqueous HCl over 7 column volumes, flow rate 5 mL/min, λ—254 nm). The purified conjugate was desalted using size exclusion chromatography (Sephadex G 25 Fine Desalting column, 0.1 M acetic acid, λ—254 nm) to afford a white solid after lyophilization. The molecular mass of the isolated peptide was confirmed by positive fragment ion distribution with the apex at 44346 amu (MALDI). Example 38 (27 mg, as the 8 acetic acid salt) gave a retention time equal to 12.19 min using size exclusion HPLC (Phenomenex BioSep-SEC-53000 column, 7.8×300 mm, 5 μm, 0.15 mM NaCl in 30 mM PBS over 20 min, pH 6.8, flow rate 0.75 mL/min, λ—215 nm).

4-1075 amu, which corresponds to a peptide with the parent molecular weight of 4298 amu (ESI-MS, LC/MS Method A). A purity of >90% was determined by LC/MS (LC/MS Method A, rt=13.68 min) for the isolated peptide (28.4 mg, as the 8 trifluoroacetic acid salt).

A mixture of Intermediate 7 (10.1 mg, 1.94 μmol) and Intermediate 2 (JenKem Technology USA Inc., 78 mg, 1.94 μmol) in 10 mL of 1×PBS buffer at pH 7.4 was stirred overnight. The reaction was then diluted with 10 mL of a solution of 20% MeOH in 10 mM aqueous HCl and purified by ion exchange chromatography (Sepharose FF Media, 0-60% 1 M NaCl in 20% methanol/10 mM aqueous HCl over 7 column volumes, flow rate 5 mL/min, λ—215 nm). The purified conjugate was desalted using size exclusion chromatography (Sephadex G 25 Fine, 50×130 mm column, 0.1 M acetic acid, λ—254 nm) to afford a white solid after lyophilization. The molecular mass of the isolated peptide was confirmed by positive fragment ion distribution with the apex at 44384 amu (MALDI). Example 39 (26.7 mg, as the 8 acetic acid salt) gave a retention time equal to 12.30 min using size exclusion HPLC (Phenomenex BioSep-SEC- Example 39

(SEQ ID NO: 42)

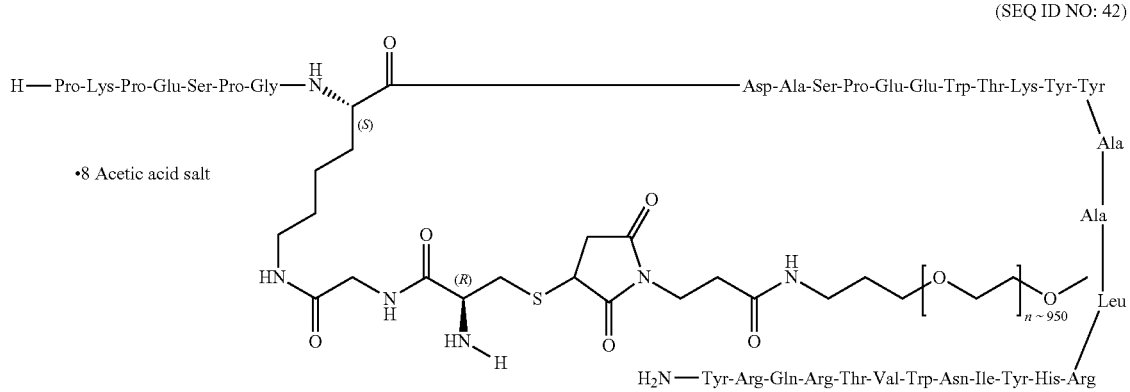

Intermediate 7 was prepared on a 40 μmol scale as a white solid using the general method, except the lysine at position 8 of the peptide was protected with an ivDde group, while proline at position 1 was protected with a Boc. After the coupling of the last amino acid (proline 1), the ivDde was removed with repeated treatments of 4% aqueous hydrazine in DMF and Fmoc-Gly-OH and Fmoc-Cys(Trt)-OH were coupled. The molecular mass of the isolated peptide was confirmed by fragment ions (M+3)/3-1433 amu and (M+4)/

53000 column, 7.8×300 mm, 5 μm, 0.15 mM NaCl in 30 mM PBS over 20 min, pH 6.8, flow rate 0.75 mL/min, λ—215 nm), and a retention time equal to 12.31 min by C18 HPLC (C18 HPLC Method A).

Example 40

(SEQ ID NO: 43)

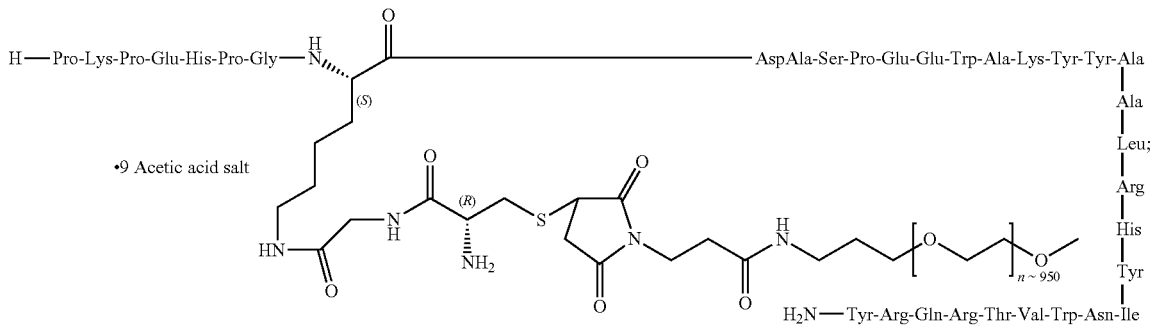

Intermediate 8 was prepared on a 40 µmol scale as a white solid using the general method, except the lysine at position 8 of the peptide was protected with an ivDde group, while proline at position 1 was protected with a Boc. After the coupling of the last amino acid (proline 1), the ivDde was removed with repeated treatments of 4% aqueous hydrazine in DMF and Fmoc-Gly-OH and Fmoc-Cys(Trt)-OH were coupled. The molecular mass of the isolated peptide was confirmed by fragment ions (M+3)/3-1440 amu and (M+4)/4-1080 amu, which corresponds to a peptide with the parent molecular weight of 4318 amu (ESI-MS, LC/MS Method A). A purity of >90% was determined by LC/MS (LC/MS Method A, rt=13.16 min) for the isolated peptide (39 mg, as the 9 trifluoroacetic acid salt).

A mixture of Intermediate 8 (10.43 mg, 1.95 µmol) and Intermediate 2 (JenKem Technology USA Inc., 86 mg, 2.15 µmol) in 10 mL of 1×PBS buffer at pH 7.4 was stirred for 2 h. The reaction was then diluted with 10 mL of a solution of 20% MeOH in 10 mM aqueous HCl and purified by ion exchange chromatography (Sepharose FF Media, 0-60% 1 M NaCl in 20% methanol/10 mM aqueous HCl over 7 column volumes, flow rate 5 mL/min, λ—215 nm). The purified conjugate was desalted using size exclusion chromatography (Sephadex G 25 Fine, 50×130 mm column, 0.1 M acetic acid, λ—254 nm) to afford a white solid after lyophilization. The molecular mass of the isolated peptide was confirmed by positive fragment ion distribution with the apex at 44514 amu (MALDI). Example 40 (35 mg, as the 9 acetic acid salt) gave a retention time equal to 14.90 min using size exclusion HPLC (Phenomenex BioSep-SEC-53000 column, 7.8×300 mm, 5 µm, 0.15 mM NaCl in 30 mM PBS over 20 min, pH 6.8, flow rate 0.75 mL/min, λ—215 nm), and a retention time equal to 12.08 min by C18 HPLC (C18 HPLC Method A).

Example 41

Intermediate 9 was prepared on a 40 µmol scale as a white solid using the general method. The molecular mass of the isolated peptide was confirmed by fragment ions (M+3)/3-1407 amu and (M+4)/4-1056 amu, which corresponds to a peptide with the parent molecular weight of 4220 amu (ESI-MS, LC/MS Method A). A purity of >90% was determined by C18 HPLC (C18 HPLC Method A, rt=8.98 min) for the isolated peptide (30 mg, as the 8 trifluoroacetic acid salt).

A mixture of Intermediate 9 (13.2 mg, 2.57 µmol) and Intermediate 2 (JenKem Technology USA Inc., 113 mg, 2.83 µmol) in 5 mL of 1×PBS buffer at pH 7.4 was shaken for 1 h, during which time the reaction became homogenous. The reaction was then diluted with 5 mL of 20% MeOH in 10 mM aqueous HCl and purified by ion exchange chromatography (Sepharose FF Media, 0-60% 1 M NaCl in 20% methanol/10 mM aqueous HCl over 7 column volumes, flow rate 5 mL/min, λ—254 nm). The purified conjugate was desalted using size exclusion chromatography (Sephadex G 25 Fine Desalting column, 0.1 M acetic acid, λ—254 nm) to afford a white solid after lyophilization. The molecular mass of the isolated peptide was confirmed by positive fragment ion distribution with the apex at 44239 amu (MALDI). Example 41 (41 mg, as the 8 acetic acid salt) gave a retention time equal to 9.20 min using size exclusion HPLC (Phenomenex BioSep-SEC-53000 column, 7.8×300 mm, 5 µm, 0.15 mM NaCl in 30 mM PBS over 20 min, pH 6.8, flow rate 0.75 mL/min, λ—215 nm).

(SEQ ID NO: 44)

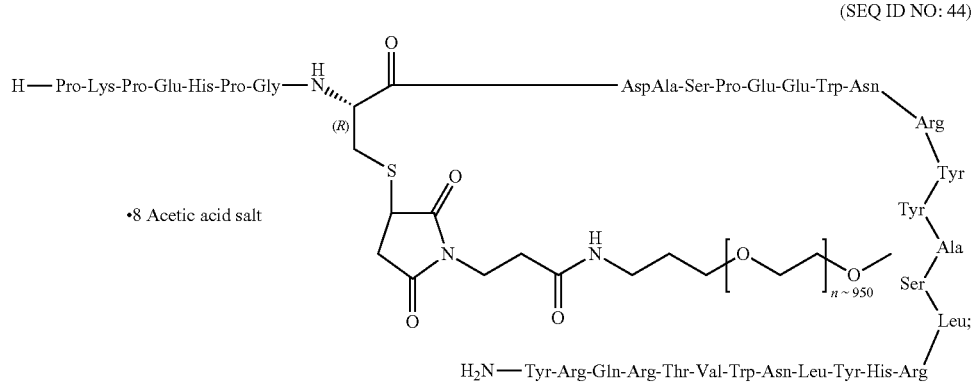

Example 42

(SEQ ID NO: 43)

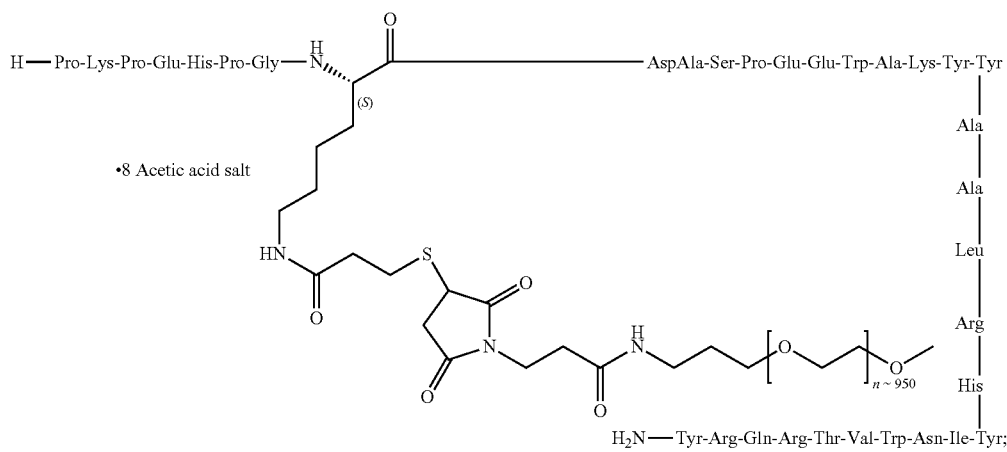

Intermediate 10 was prepared on a 40 µmol scale as a white solid using the general method, except the lysine at position 8 of the peptide was protected with an ivDde group, while proline 1 was protected with a Boc. After the coupling of the last amino acid (proline 1), the ivDde was removed with repeated treatments of 4% aqueous hydrazine in DMF and Trt-mercaptopropionic acid (MPA) was coupled. The molecular mass of the isolated peptide was confirmed by fragment ions (M+3)/3-1416 amu and (M+4)/4-1062 amu, which corresponds to a peptide with the parent molecular weight of 4246 amu (ESI-MS, LC/MS Method A). A purity of >90% was determined by LC/MS (LC/MS Method A, rt=13.88 min) for the isolated peptide (22.2 mg, as the 8 trifluoroacetic acid salt).

A mixture of Intermediate 10 (10.2 mg, 1.98 µmol) and Intermediate 2 (JenKem Technology USA Inc., 87 mg, 2.18 µmol) in 10 mL of 1×PBS buffer at pH 7.4 was stirred overnight. The reaction was then diluted with 10 mL of a solution of 20% MeOH in 10 mM aqueous HCl and purified by ion exchange chromatography (Sepharose FF Media, 0-60% 1 M NaCl in 20% methanol/10 mM aqueous HCl over 7 column volumes, flow rate 5 mL/min, λ—215 nm). The purified conjugate was desalted using size exclusion chromatography (Sephadex G 25 Fine, 50×130 mm column, 0.1 M acetic acid, λ—254 nm) to afford a white solid after lyophilization. The molecular mass of the isolated peptide was confirmed by positive fragment ion distribution with the apex at 44392 amu (MALDI). Example 42 (32.2 mg, as the 8 acetic acid salt) gave a retention time equal to 13.83 min using size exclusion HPLC (Phenomenex BioSep-SEC-53000 column, 7.8×300 mm, 5 µm, 0.15 mM NaCl in 30 mM PBS over 20 min, pH 6.8, flow rate 0.75 mL/min, λ—215 nm), and a retention time equal to 12.06 min by C18 HPLC (C18 HPLC Method A).

Example 43

(SEQ ID NO: 45)

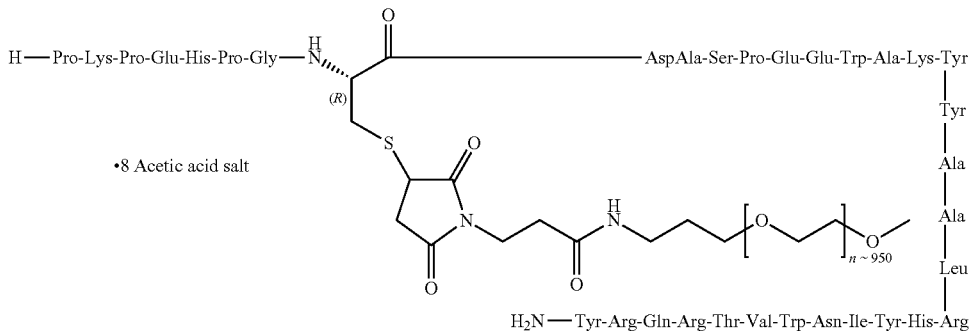

Intermediate 11 was prepared on a 35 µmol scale as a white solid using the general method. The molecular mass of the isolated peptide was confirmed by fragment ions (M+3)/3-1378 amu and (M+4)/4-1034 amu, which corresponds to a peptide with the parent molecular weight of 4133 amu (ESI-MS, LC/MS Method A). A purity of >90% was determined by LC/MS (LC/MS Method A, rt=13.77 min) for the isolated peptide (13 mg, as the 8 trifluoroacetic acid salt).

A mixture of Intermediate 11 (9.54 mg, 1.89 µmol) and Intermediate 2 (JenKem Technology USA Inc., 83 mg, 2.08

µmol) in 10 mL of a solution of 1×PBS buffer at pH 7.4 was stirred at ambient temperature overnight. The reaction was then diluted with 10 mL of a solution of 20% MeOH in 10 mM aqueous HCl and purified by ion exchange chromatography (Sepharose FF Media, 0-60% 1 M NaCl in 20% methanol/10 mM aqueous HCl over 7 column volumes, flow rate 5 mL/min, λ—215 nm). The purified conjugate was desalted using size exclusion chromatography (Sephadex G 25 Fine, 50×130 mm column, 0.1 M acetic acid, λ—254 nm) to afford a white solid after lyophilization. The molecular mass of the isolated peptide was confirmed by positive fragment ion distribution with the apex at 44117 amu (MALDI). Example 43 (32 mg, as the 8 acetic acid salt) gave a retention time equal to 10.65 min using size exclusion HPLC (Phenomenex BioSep-SEC-53000 column, 7.8×300 mm, 5 µm, 0.15 mM NaCl in 30 mM PBS over 20 min, pH 6.8, flow rate 0.75 mL/min, λ—215 nm), and a retention time equal to 12.10 min by C18 HPLC (C18 HPLC Method A).

BIOLOGICAL EXAMPLES

Potency of PYY Analogs at the Human Neuropeptide Y Receptor Type 2

The relative potency of PYY analogs at the human Neuropeptide Y receptor type 2 was determined using a melanophore assay essentially as described in Jayawickreme et al. (2005) *Current Protocols in Pharmacology* 12.9.1-12.

Effects of PYY Analogs on Food Intake

Cumulative food intake after 6 h was determined for the PYY analogs in either lean (Model A) or diet-induced obese (DIO) (Model B) C57BL/6 mice in a BioDaQ system for continuous monitoring of food intake (Research Diets Inc., New Brunswick, N.J.). Model A utilized 10 week old male C57BL/6 mice (Taconic, Germantown, N.Y.) fed a normal chow (Purina PMI 5001) whereas Model B utilized 25 week old male C57BL/6 mice fed a 45% high fat chow for 20 weeks (Research Diets D12451). Mice were placed singly into the BioDaQ cages and acclimatized for a minimum of 6 days and were allowed ad libitum access to food and water. Approximately 1 hour prior to lights-out, animals were dosed subcutaneously with either vehicle (20 mM Acetate buffer, pH 4.9 or 20% DMSO in water) or analogs dissolved in vehicle (1 mg/kg) (8 animals per group). Once all animals have been dosed, feeder gates were opened providing ad-libitum access to food. Continuous food intake was monitored and collected for 15 hours. Hourly food intake, as well as 6 and 15-hour cumulative food intake, was summarized as % inhibition relative to vehicle controls. The data were analyzed in JMP 6.0.0 (SAS Institute, Cary, N.C.) using a pooled variance t-test vs. groups treated with human PYY (3-36)$NH_2$. P-values <0.05 were considered to indicate a significant difference between treatment groups.

Table 1 shows potency at the human Neuropeptide Y receptor and food intake reduction for the PYY analogs shown in Examples 1-35.

TABLE 1

| Example | hNPY Y2 $pEC_{50}$ | % reduction in food intake, model A | % reduction in food intake, model B | p value (pooled variance t-test vs hPYY[3-36]) |
|---|---|---|---|---|
| Example 1 | 9.9 | −81 | | <0.0001 |
| Example 2 | 9.8 | −50 | | 0.0038 |
| Example 3 | 9.5 | −89 | | <0.0001 |
| Example 4 | 10.7 | −83 | | <0.0001 |
| Example 5 | 10.5 | −89 | | <0.0001 |
| Example 6 | 10.1 | −88 | | <0.0001 |
| Example 7 | 10.1 | −91 | | <0.0001 |
| Example 8 | 10.7 | −74 | | <0.0001 |
| Example 9 | 10.7 | −86 | | <0.0001 |
| Example 10 | 10.4 | −88 | | <0.0001 |
| Example 11 | 10.3 | −86 | | <0.0001 |
| Example 12 | 10.2 | −88 | | <0.0001 |
| Example 13 | 9.9 | −85 | | <0.0001 |
| Example 14 | 10.5 | −89 | | <0.0001 |
| Example 15 | 10 | −90 | | <0.0001 |
| Example 16 | 10.4 | −90 | | <0.0001 |
| Example 17 | 9.9 | −90 | | <0.0001 |
| Example 18 | 10.5 | −92 | | <0.0001 |
| Example 19 | 10.2 | −89 | | <0.0001 |
| Example 20 | 10.5 | −86 | | <0.0001 |
| Example 21 | 10.5 | −90 | | <0.0001 |
| Example 22 | 10.2 | | −80 | <0.0001 |
| Example 23 | 9.8 | | −86 | <0.0001 |
| Example 24 | 10.6 | | −56 | 0.0035 |
| Example 25 | 9.6 | | −68 | 0.0003 |
| Example 26 | 9.7 | | −81 | <0.0001 |
| Example 27 | 9.8 | | −69 | <0.0001 |
| Example 28 | 10 | | −65 | <0.0001 |
| Example 29 | 9.7 | | −54 | 0.0006 |
| Example 30 | 9.7 | | −73 | <0.0001 |
| Example 31 | 9.8 | −59 | | 0.0004 |
| Example 32 | 10.1 | | −77 | <0.0001 |
| Example 33 | 10 | | −67 | <0.0001 |
| Example 34 | 10 | | −69 | <0.0001 |
| Example 35 | 10.3 | | −70 | <0.0001 |

Table 2 shows examples of PYY analogs which have potency at the human Neuropeptide Y receptor but do not show food intake reduction greater than human PYY(3-36)$NH_2$ at the 6 h time point.

TABLE 2

| Peptide | Peptide Sequence | hNPY Y2 $pEC_{50}$ | % reduction in food intake, model A | SEQ ID NO |
|---|---|---|---|---|
| Peptide 1 | PKPEAPGCDASPEEWNRYYASLRKYLNWVTRQNY-$NH_2$ | 7.9 | 5 | 46 |
| Peptide 2 | IKPEAPLSKQLEEEAVRYYASLRHYLNLVTRQRY-$NH_2$ | 8.6 | −12 | 47 |
| Peptide 3 | PKPEAPGEDASPKEWNRYYASLRKYLNWVTRQRY-$NH_2$ | 9.2 | −30 | 48 |
| Peptide 4 | PKPEHPGEDASPEELNRYHAALRAYLNLVTRQRY-$NH_2$ | 11.1 | −26 | 49 |

TABLE 2-continued

| Peptide | Peptide Sequence | hNPY Y2 $pEC_{50}$ | % reduction in food intake, model A | SEQ ID NO |
|---|---|---|---|---|
| Peptide 5 | PKPEHPGEDASPEELNRYYAALRAYLNLVTRQKY-NH$_2$ | 8.5 | -7 | 50 |
| Peptide 6 | PKPEHPGEDASPEELNRYYAALRAYLNLVTKQRY-NH$_2$ | 9.7 | -14 | 51 |
| Peptide 7 | PQPESPGCNASPEELAKYHAALRHYVNLITRQRY-NH$_2$ | 10.2 | -25 | 52 |
| Peptide 8 | IKPPYPGCDASPEEQNKYYASLRAYWNLVTRQRY-NH$_2$ | 9.3 | -19 | 53 |
| Peptide 9 | PKPESPGSNASPEDWAKYQAAVRHYVNLITRQRY-NH$_2$ | 10.6 | -24 | 54 |
| Peptide 10 | PEPEHPGCDASPEDQNKYHASLRKYLNWVTRQRY-NH$_2$ | 9.5 | -21 | 55 |
| Peptide 11 | IKPPEPGCDASPEEQNKYYASLRHYWNLVTRQRY-NH$_2$ | 9.5 | -5 | 56 |
| Peptide 12 | IEPEAPGEDASPEELNRYYASLRHYLNLVTRQRY-NH$_2$ | 9.8 | -15 | 57 |
| Peptide 13 | PKPESPGSDASPEDLAKYHAAVRHYVNLITRQRY-NH$_2$ | 10.9 | -23 | 58 |
| Peptide 14 | PKPEAPGCDASPEEWNRYYASLRKYLNWVTRQHY-NH$_2$ | 8.2 | 24 | 59 |
| Peptide 15 | PKPVAPGCDASPAELNRQYSDLRNYWNLVTRQRY-NH$_2$ | 8.9 | -17 | 60 |
| Peptide 16 | IQPEAPGEDASPEELNRYYASLRHYLNLVTRQRY-NH$_2$ | 10 | -32 | 61 |
| Peptide 17 | PKPESPGKDASPEDLAKYHAAVRHYVNLITRQRY-NH$_2$ | 11 | -36 | 62 |
| Peptide 18 | PQPESPEGNASPEDWACYHAAVRHYVNLITRQRY-NH$_2$ | 9.7 | -17 | 63 |
| Peptide 19 | IHPEAPGEDASPEELNRYYASLRHYLNLVTRQRY-NH$_2$ | 10 | -26 | 64 |
| Peptide 20 | IKPEAPGEDASPEQLMAQYASLRHYLNLVTRQRY-NH$_2$ | 9.9 | -16 | 65 |
| Peptide 21 | PKPEAPLSKQLEEEAVRYYASLRHYLNLVTRQRY-NH$_2$ | 8.7 | -2 | 66 |
| Peptide 22 | PKPEAPGCDASPEELNRYQASLRHYLNLVTRQRY-NH$_2$ | 10.3 | -16 | 67 |

Effects of Example 5 in Combination with Exendin-4 on Body Weight, Body Composition and Food Intake Reduction A chronic (41 days) in vivo efficacy study was conducted in a rodent model for obesity (diet-induced obese (DIO) Long Evans rat) to investigate the efficacy and durability of Example 5 singly and in combination with exendin-4 as anti-obesity agents.

Male Diet-Induced Obese (DIO) Long Evans (LE) rats were used (Harlan Laboratories, Inc., Indianapolis, Ind.) and beginning at weaning (about 3 weeks of age), the rats were fed a high fat chow (Teklad TD 95217, 40% kcal from fat, Harlan Laboratories, Madison, Wis.). Rats were 17 weeks old at the start of the study. The rats were housed 1 per cage and given ad libitum access to TD.95217 chow and water, maintained on a 12 h light/dark cycle from 5:00 AM to 5:00 PM at 21° C. and 50% relative humidity and allowed to acclimate for at least 7 days prior to baseline measurements. Baseline fat mass and non-fat mass measurements were taken 3 days before the start of peptide infusion and on day 40 of treatment using a QMR instrument (Echo Medical Systems, Houston, Tex.). Rats were randomized according to their percent body fat mass into 6 groups: (1) vehicle (sterile water, n=8), (2) Exendin-4 ($ED_{50}$=0.15 mg/kg/day, n=8), (3) Example 5 ($ED_{50}$=0.03 mg/kg/day, n=8), (4) PYY(3-36)NH$_2$ (1.5 mg/kg/day, n=8), (5) Exendin-4+Example 5 (n=8) and (6) Exendin-4+PYY(3-36)NH$_2$ (n=8). AlZET® mini-osmotic pumps (6 week; Model 2006, Durect Corporation, Cupertino, Calif.) were filled under sterile condition with either vehicle or peptide one day prior to the surgery. Each rat was implanted with two osmotic pumps subcutaneously in the scapula region containing vehicle or peptide according to their treatment group. Body weight and food intake were measured twice per week beginning three days before the 41-day treatment period. On day 41 of treatment, whole blood was collected by cardiac stick under isoflurane anesthesia. Plasma and serum were then prepared from the whole blood for serum chemistry analysis. All the data are presented as mean±SEM. The data were analyzed in either Prism (GraphPad Software, Inc., La Jolla, Calif.) or Excel using a Student's T-test to compare each group to the appropriate control group. P-values <0.05 were considered to indicate a significant difference between treatment groups.

All procedures were performed in compliance with the Animal Welfare Act, USDA regulations and approved by the GlaxoSmithKline Institutional Animal Care and Use Committee.

In DIO rats, administration of Example 5 at the $ED_{50}$ for weight loss for 40 days resulted in -6.1% (p<0.05) weight loss whereas native PYY(3-36)NH$_2$ at the $ED_{50}$ resulted in -1.3% (p=0.46) weight loss vs. vehicle (FIG. 1). The combination of Example 5 and exendin-4 at combo $ED_{50}$ doses for 40 days resulted in sustained and significant weight loss of -30.9% vs. vehicle (p<0.05), which far exceeded the expected additive effect based on weight loss of exendin-4 and Example 5 when administered alone (-11.3% and -6.1%, respectively, with a projected additive weight loss of -17.4%). Whereas, native PYY(3-36)NH$_2$ in combination with exendin-4 resulted in −10.2% weight loss vs. vehicle which was sub-additive based on weight loss of exendin-4 and PYY(3-36)NH$_2$ when administered alone (−11.3% and −1.3%, with a projected additive weight loss of −12.6%).

Figure 2:
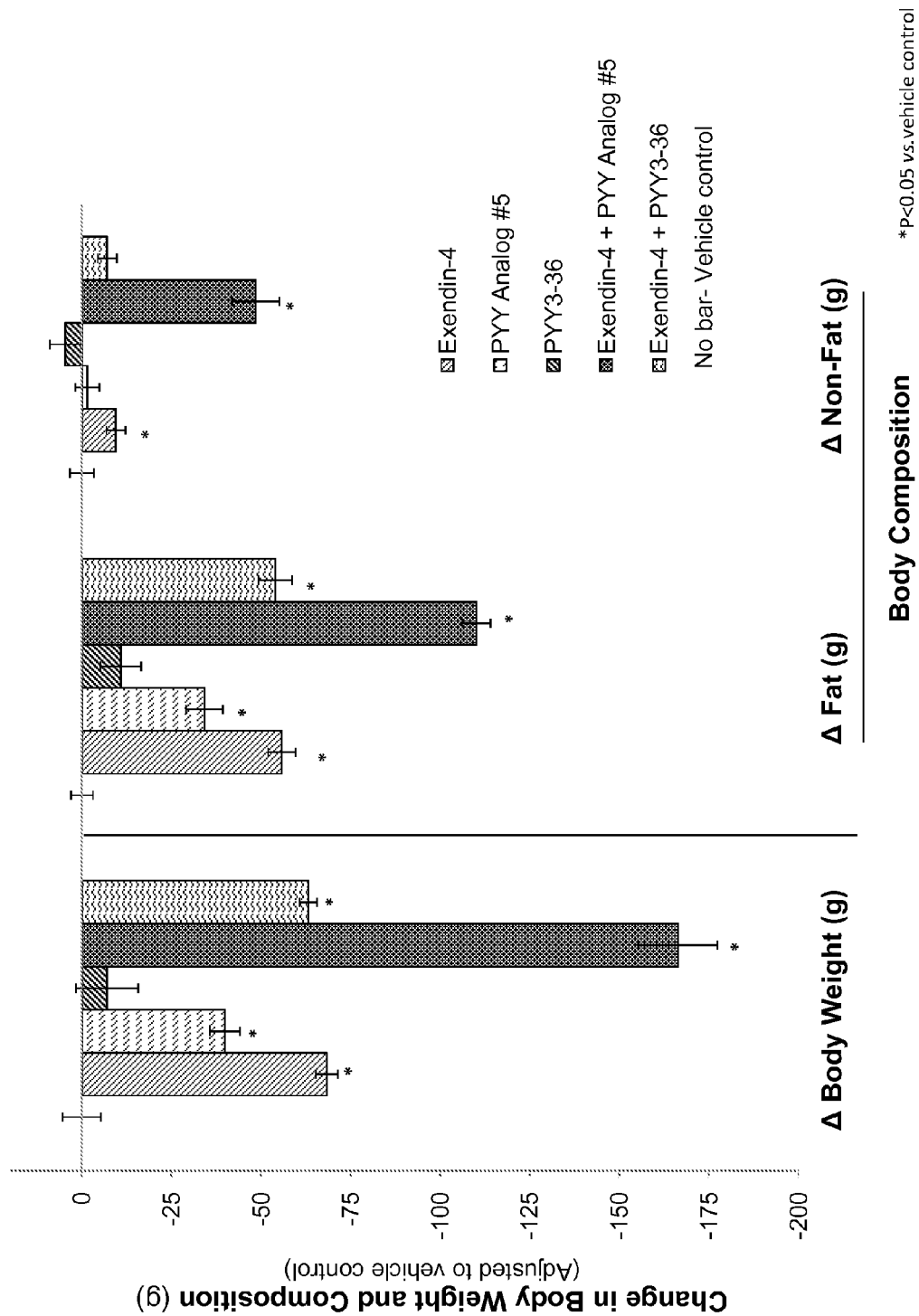
FIG. 2 shows the effects of the peptide shown in Example 5 (Analog #5), PYY(3-36)NH$_2$(PYY3-36), and exendin-4 singly and in combination on body composition changes in DIO LE rats.

Changes in body composition were primarily driven by loss of body fat mass, with some changes in non-fat mass and mirrored the body weight changes in all treatment groups (FIG. 2). Specifically, the animals treated with Example 5 lost −34.2 grams of fat mass from vehicle control ($p<0.05$), the PYY(3-36)NH$_2$ animals lost −10.9 grams fat mass ($p=0.12$ vs. vehicle control) and animals treated with exendin-4 lost −55.8 grams fat mass ($p<0.05$ vs. vehicle control) during the treatment period. The Example 5+ exendin-4 combination had a more than additive effect on fat mass where the combination lost −110.1 grams ($p<0.05$ vs. vehicle control), which was significantly greater than the predicted additivity value of −90 grams ($p<0.05$) (FIG. 3). In contrast, PYY(3-36)NH$_2$ in combination with exendin-4 resulted in −54.0 grams fat mass loss vs. vehicle ($p<0.05$) which was less than the predicted additivity value of −66.7 grams.

In addition, a −57.1% inhibition of cumulative food intake ($p<0.05$ vs. vehicle control) was observed when Example 5 was co-administered with exendin-4 compared with −18.8% inhibition ($p=0.87$ vs. vehicle control) with the PYY(3-36)NH$_2$+ exendin-4 combination. There appears to be a more than additive efficacy with the Example 5+ exendin-4 combination based upon the food intake inhibition of each peptide administered alone (−11.5% and −20.1%, respectively, with a projected additive food intake inhibition of −31.6%). In contrast, the native PYY(3-36)NH$_2$+ exendin-4 combination resulted in sub-additive food intake inhibition based upon the food intake inhibition of each peptide administered alone (−0.7% for PYY(3-36)NH$_2$ and −20.1% for exendin-4, with a projected additive food intake inhibition of −20.8%).

Example 23 in Combination with Exendin-4 Causes More than Additive Effects on Glucose Parameters in Diabetic ZDF Rats A chronic (26 days) in vivo efficacy study was conducted in a rodent model for diabetes (Zucker Diabetic Fatty (ZDF) rat) to investigate the efficacy and durability of Example 23 singly and in combination with exendin-4 as anti-diabetes agents.

Male ZDF rats were 12 weeks old at the start of the study (Charles River, Inc., Boston, Mass.). The ZDF rats were housed 1 per cage and given ad libitum access to diet (Purina PMI 5008) and water, maintained on a 12 hr light/dark cycle from 5:00 AM to 5:00 PM at 21° C. and 50% relative humidity and allowed to acclimate for at least 6 days prior to baseline measurements and 10 days prior to the surgeries. Baseline fat mass and non-fat mass measurements were taken 3 days before the start of peptide infusion and on day 26 of treatment using a QMR instrument (Echo Medical Systems, Houston, Tex.). Blood samples were taken via tail snip to measure fed glucose values and % HbA1c values two days before the start of drug dosing; this data was used to randomize the animals into 7 groups: (1) Lean vehicle control (sterile phosphate buffered saline (PBS), pH 4.9, n=8), (2) ZDF vehicle control (sterile PBS, pH 4.9, n=8), (3) Exendin-4 ($ED_{20}$=0.0055 mg/kg/day, n=8), (4) Example 23 ($ED_{20}$=0.02 mg/kg/day, n=8), (5) PYY(3-36)NH$_2$(0.02 mg/kg/day, n=8), (6) Exendin-4+ Example 23 (n=4) and (7) Exendin-4+PYY(3-36)NH$_2$ (n=8). ALZET® mini-osmotic pumps (4-week; Model 2006, Durect Corporation, Cupertino, Calif.) were filled under sterile condition with either vehicle or peptide one day prior to the surgery. Similar surgical implantation of the mini-pumps was performed as described for the DIO rats above (except animals were injected ID with lidocaine (0.1 mL of 0.125% lidocaine). Body weight and food intake were measured twice per week beginning 3 days before the 26-day treatment period. On day 26 of treatment, whole blood was collected by cardiac stick under isoflurane anesthesia. The whole blood was used to determine the % HbA1c and the serum was used to measure glucose. The data were analyzed in either Prism (GraphPad Software, Inc., La Jolla, Calif.) or Excel using a Student's T-test to compare each group to the appropriate control group. P-values <0.05 were considered to indicate a significant difference between treatment groups.

All procedures were performed in compliance with the Animal Welfare Act, USDA regulations and approved by the GlaxoSmithKline Institutional Animal Care and Use Committee.

Table 3 shows the glucose and glycosylated HbA1c changes from baseline and from vehicle control ZDF animals ($\Delta\Delta$) following chronic treatment (26 days) with Example 23, PYY(3-36)NH$_2$, or exendin-4 singly or in combination. Singly, only the exendin-4 and Example 23 achieved statistically significant glucose lowering from vehicle control ($\Delta\Delta$ −53.9 and −54.5 mg/dL, respectively; $p<0.05$) compared to PYY(3-36)NH$_2$($\Delta\Delta$ −33.1; $p=0.11$). Treatment with the combination of Example 23 and exendin-4 combo at $ED_{20}$ doses for HbA1c lowering for 26 days resulted in significant glucose lowering $\Delta\Delta$ −152.3 mg/dL ($p<0.05$ vs. vehicle control), which exceeded the expected additive effect based on glucose lowering of exendin-4 and Example 23 when administered alone ($\Delta\Delta$ −53.9 and −54.5 mg/dL, with a projected additive glucose lowering of −108.4 mg/dL vs. vehicle control). The $\Delta\Delta$% HbA1c levels closely mirrored the glucose changes in all treatment groups, however, none of the groups were deemed statistically significant.

TABLE 3

Changes in glucose and HbA1c after 26 days of treatment with Example 23 and/or exendin-4 singly and in combination in ZDF rats

| Treatment Group | $\Delta\Delta$Glucose | $\Delta\Delta$ % HbA1c |
| --- | --- | --- |
| Exendin-4 | −53.9 ± 18.3 | −0.4 ± 0.2 |
| Example 23 | −54.5 ± 13.7 | −0.4 ± 0.2 |
| PYY(3-36)NH$_2$ | −33.1 ± 17 | 0.01 ± 0.4 |
| Ex-4 + Example 23 | −152.3 ± 91.5 | −1.3 ± 0.8 |
| Ex-4 + PYY(3-36)NH$_2$ | −17.6 ± 24.4 | −0.4 ± 0.3 |

$\Delta\Delta$ = Change in parameter from baseline and vehicle control
Bold = $p < 0.05$ from vehicle control

That which is claimed:

1. A polypeptide comprising the amino acid sequence:
ProLysProGluAlaProGlyLysAspAlaSerProGluGlu-TrpAsnArgTyrTyrAla AspLeuArgHisTyrLeuAsn-TrpLeuThrArgGlnArgTyr (SEQ ID NO:38).

2. A pharmaceutical combination comprising a polypeptide according to claim 1 and exendin-4.

3. A pharmaceutical combination comprising a polypeptide according to claim 1 and GLP-1.

4. A pharmaceutical composition comprising a polypeptide according to claim 1 and a pharmaceutically acceptable carrier.

5. A method of treating Type 2 Diabetes Mellitus in a human subject, said method comprising administering a polypeptide according to claim 1 to a subject in need thereof.

6. The method according to claim 5, wherein 0.05-100 µg of the polypeptide is administered to the subject per day.

7. A method of treating obesity in a human subject, said method comprising administering a polypeptide according to claim 1 to a subject in need thereof.

8. The method according to claim 7, wherein 0.05-100 µg of the polypeptide is administered to the subject per day.

9. A pharmaceutical combination comprising a polypeptide according to claim 2 and exendin-4.

10. A polypeptide consisting of the amino acid sequence:
ProLysProGluAlaProGlyLysAspAlaSerProGluGlu-TrpAsnArgTyrTyrAla AspLeuArgHisTyrLeuAsn-TrpLeuThrArgGlnArgTyr (SEQ ID NO:38).

11. A pharmaceutical combination comprising a polypeptide according to claim 10 and exendin-4.

12. A pharmaceutical combination comprising a polypeptide according to claim 10 and GLP-1.

13. A pharmaceutical composition comprising a polypeptide according to claim 10 and a pharmaceutically acceptable carrier.

14. A method of treating Type 2 Diabetes Mellitus in a human subject, said method comprising administering a polypeptide according to claim 10 to a subject in need thereof.

15. The method according to claim 14, wherein 0.05-100 µg of the polypeptide is administered to the subject per day.

16. A method of treating obesity in a human subject, said method comprising administering a polypeptide according to claim 10 to a subject in need thereof.

17. The method according to claim 16, wherein 0.05-100 µg of the polypeptide is administered to the subject per day.

18. A polypeptide consisting of the amino acid sequence:
ProLysProGluAlaProGlyLysAspAlaSerProGluGlu-TrpAsnArgTyrTyrAla AspLeuArgHisTyrLeuAsn-TrpLeuThrArgGlnArgTyr-NH2 (SEQ ID NO:7).

19. A pharmaceutical combination comprising a polypeptide according to claim 18 and exendin-4.

20. A pharmaceutical combination comprising a polypeptide according to claim 18 and GLP-1.

21. A pharmaceutical composition comprising a polypeptide according to claim 18 and a pharmaceutically acceptable carrier.

22. A method of treating Type 2 Diabetes Mellitus in a human subject, said method comprising administering a polypeptide according to claim 18 to a subject in need thereof.

23. The method according to claim 22, wherein 0.05-100 µg of the polypeptide is administered to the subject per day.

24. A method of treating obesity in a human subject, said method comprising administering a polypeptide according to claim 18 to a subject in need thereof.

25. The method according to claim 24, wherein 0.05-100 µg of the polypeptide is administered to the subject per day.

26. A salt form of the polypeptide consisting of:
ProLysProGluAlaProGlyLysAspAlaSerProGluGlu-TrpAsnArgTyrTyrAla AspLeuArgHisTyrLeuAsn-TrpLeuThrArgGlnArgTyr-NH2 (SEQ ID NO:7).

27. The polypeptide according to claim 26, wherein said salt is an acetate salt.

28. The polypeptide according to claim 26, wherein said salt is the acetic acid salt.

29. A pharmaceutical combination comprising a polypeptide according to claim 26 and GLP-1.

30. A pharmaceutical composition comprising a polypeptide according to claim 26 and a pharmaceutically acceptable carrier.

31. A method of treating Type 2 Diabetes Mellitus in a human subject, said method comprising administering a polypeptide according to claim 26 to a subject in need thereof.

32. A method of treating obesity in a human subject, said method comprising administering a polypeptide according to claim 26 to a subject in need thereof.

33. A pharmaceutical combination comprising an acetate salt form of the polypeptide comprising:
ProLysProGluAlaProGlyLysAspAlaSerProGluGlu-TrpAsnArgTyrTyrAla AspLeuArgHisTyrLeuAsn-TrpLeuThrArgGlnArgTyr (SEQ ID NO:38) and exendin-4.

34. A method of treating Type 2 Diabetes Mellitus in a human subject, said method comprising administering the pharmaceutical combination according to claim 33 to a subject in need thereof.

35. A method of treating obesity in a human subject, said method comprising administering the pharmaceutical combination according to claim 33 to a subject in need thereof.

36. A pharmaceutical combination comprising an acetate salt form of the polypeptide comprising:
ProLysProGluAlaProGlyLysAspAlaSerProGluGlu-TrpAsnArgTyrTyrAla AspLeuArgHisTyrLeuAsn-TrpLeuThrArgGlnArgTyr-NH2 (SEQ ID NO: 7) and exendin-4.

37. A method of treating Type 2 Diabetes Mellitus in a human subject, said method comprising administering the pharmaceutical combination according to claim 36 to a subject in need thereof.

38. A method of treating obesity in a human subject, said method comprising administering the pharmaceutical combination according to claim 36 to a subject in need thereof.

* * * * *

SEQUENCE LISTING

<160> NUMBER OF SEQ ID NOS: 67

<210> SEQ ID NO 1
<211> LENGTH: 34
<212> TYPE: PRT

```
<213> ORGANISM: Artificial Sequence
<220> FEATURE:
<223> OTHER INFORMATION: PYY ANALOG
<220> FEATURE:
<221> NAME/KEY: MISC_FEATURE
<222> LOCATION: (5)..(5)
<223> OTHER INFORMATION: X = A, H, or S
<220> FEATURE:
<221> NAME/KEY: MISC_FEATURE
<222> LOCATION: (8)..(8)
<223> OTHER INFORMATION: X = E or K
<220> FEATURE:
<221> NAME/KEY: MISC_FEATURE
<222> LOCATION: (12)..(12)
<223> OTHER INFORMATION: X = P or A
<220> FEATURE:
<221> NAME/KEY: MISC_FEATURE
<222> LOCATION: (15)..(15)
<223> OTHER INFORMATION: X = L or W
<220> FEATURE:
<221> NAME/KEY: MISC_FEATURE
<222> LOCATION: (16)..(16)
<223> OTHER INFORMATION: X = N, A, or T
<220> FEATURE:
<221> NAME/KEY: MISC_FEATURE
<222> LOCATION: (17)..(17)
<223> OTHER INFORMATION: X = R or K
<220> FEATURE:
<221> NAME/KEY: MISC_FEATURE
<222> LOCATION: (21)..(21)
<223> OTHER INFORMATION: X = S, D, or A
<220> FEATURE:
<221> NAME/KEY: MISC_FEATURE
<222> LOCATION: (24)..(24)
<223> OTHER INFORMATION: X = H or K
<220> FEATURE:
<221> NAME/KEY: MISC_FEATURE
<222> LOCATION: (26)..(26)
<223> OTHER INFORMATION: X = L or I
<220> FEATURE:
<221> NAME/KEY: MISC_FEATURE
<222> LOCATION: (29)..(29)
<223> OTHER INFORMATION: X =  V or L

<400> SEQUENCE: 1

Pro Lys Pro Glu Xaa Pro Gly Xaa Asp Ala Ser Xaa Glu Glu Xaa Xaa
1               5                   10                  15

Xaa Tyr Tyr Ala Xaa Leu Arg Xaa Tyr Xaa Asn Trp Xaa Thr Arg Gln
            20                  25                  30

Arg Tyr

<210> SEQ ID NO 2
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MISC_FEATURE
<222> LOCATION: (5)..(5)
<223> OTHER INFORMATION: X = A, H, or S
<220> FEATURE:
<221> NAME/KEY: MISC_FEATURE
<222> LOCATION: (8)..(8)
<223> OTHER INFORMATION: X = E or K
<220> FEATURE:
<221> NAME/KEY: MISC_FEATURE
<222> LOCATION: (12)..(12)
<223> OTHER INFORMATION: X = P or A
<220> FEATURE:
<221> NAME/KEY: MISC_FEATURE
<222> LOCATION: (15)..(15)
<223> OTHER INFORMATION: X = L or W
<220> FEATURE:
<221> NAME/KEY: MISC_FEATURE
```

```
<222> LOCATION: (16)..(16)
<223> OTHER INFORMATION: X = N, A, or T
<220> FEATURE:
<221> NAME/KEY: MISC_FEATURE
<222> LOCATION: (17)..(17)
<223> OTHER INFORMATION: X = R or K
<220> FEATURE:
<221> NAME/KEY: MISC_FEATURE
<222> LOCATION: (21)..(21)
<223> OTHER INFORMATION: X = S, D, or A
<220> FEATURE:
<221> NAME/KEY: MISC_FEATURE
<222> LOCATION: (24)..(24)
<223> OTHER INFORMATION: X = H or K
<220> FEATURE:
<221> NAME/KEY: MISC_FEATURE
<222> LOCATION: (26)..(26)
<223> OTHER INFORMATION: X = L or I
<220> FEATURE:
<221> NAME/KEY: MISC_FEATURE
<222> LOCATION: (29)..(29)
<223> OTHER INFORMATION: X = V or L
<220> FEATURE:
<221> NAME/KEY: MOD_RES
<222> LOCATION: (34)..(34)
<223> OTHER INFORMATION: AMIDATION

<400> SEQUENCE: 2

Pro Lys Pro Glu Xaa Pro Gly Xaa Asp Ala Ser Xaa Glu Glu Xaa Xaa
1               5                   10                  15

Xaa Tyr Tyr Ala Xaa Leu Arg Xaa Tyr Xaa Asn Trp Xaa Thr Arg Gln
            20                  25                  30

Arg Tyr

<210> SEQ ID NO 3
<211> LENGTH: 34
<212> TYPE: PRT
<213> ORGANISM: Artificial Sequence
<220> FEATURE:
<223> OTHER INFORMATION: PYY Analog
<220> FEATURE:
<221> NAME/KEY: MOD_RES
<222> LOCATION: (34)..(34)
<223> OTHER INFORMATION: AMIDATION

<400> SEQUENCE: 3

Pro Lys Pro Glu Ala Pro Gly Lys Asp Ala Ser Pro Glu Glu Leu Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 4
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 4

Pro Lys Pro Glu Ala Pro Gly Lys Asp Ala Ser Pro Glu Glu Leu Asn
1               5                   10                  15

Arg Tyr Tyr Ala Ser Leu Arg Lys Tyr Leu Asn Trp Leu Thr Arg Gln
            20                  25                  30
```

Arg Tyr

<210> SEQ ID NO 5
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 5

Pro Lys Pro Glu Ala Pro Gly Lys Asp Ala Ser Pro Glu Glu Leu Asn
1               5                   10                  15
Arg Tyr Tyr Ala Ser Leu Arg His Tyr Leu Asn Trp Leu Thr Arg Gln
            20                  25                  30
Arg Tyr

<210> SEQ ID NO 6
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 6

Pro Lys Pro Glu Ala Pro Gly Lys Asp Ala Ser Pro Glu Glu Trp Asn
1               5                   10                  15
Arg Tyr Tyr Ala Asp Leu Arg Lys Tyr Leu Asn Trp Leu Thr Arg Gln
            20                  25                  30
Arg Tyr

<210> SEQ ID NO 7
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 7

Pro Lys Pro Glu Ala Pro Gly Lys Asp Ala Ser Pro Glu Glu Trp Asn
1               5                   10                  15
Arg Tyr Tyr Ala Asp Leu Arg His Tyr Leu Asn Trp Leu Thr Arg Gln
            20                  25                  30
Arg Tyr

<210> SEQ ID NO 8
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

```
<400> SEQUENCE: 8

Pro Lys Pro Glu Ala Pro Gly Lys Asp Ala Ser Pro Glu Glu Trp Asn
1               5                   10                  15

Arg Tyr Tyr Ala Ser Leu Arg Lys Tyr Leu Asn Trp Leu Thr Arg Gln
            20                  25                  30

Arg Tyr

<210> SEQ ID NO 9
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 9

Pro Lys Pro Glu Ala Pro Gly Lys Asp Ala Ser Pro Glu Glu Trp Asn
1               5                   10                  15

Arg Tyr Tyr Ala Ser Leu Arg His Tyr Leu Asn Trp Leu Thr Arg Gln
            20                  25                  30

Arg Tyr

<210> SEQ ID NO 10
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 10

Pro Lys Pro Glu Ala Pro Gly Lys Asp Ala Ser Pro Glu Glu Trp Asn
1               5                   10                  15

Arg Tyr Tyr Ala Asp Leu Arg Lys Tyr Leu Asn Trp Val Thr Arg Gln
            20                  25                  30

Arg Tyr

<210> SEQ ID NO 11
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 11

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Val Thr Arg Gln
            20                  25                  30

Arg Tyr

<210> SEQ ID NO 12
```

```
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 12
```

Pro Lys Pro Glu Ala Pro Gly Lys Asp Ala Ser Pro Glu Glu Trp Asn
1               5                   10                  15

Arg Tyr Tyr Ala Ser Leu Arg Lys Tyr Leu Asn Trp Val Thr Arg Gln
            20                  25                  30

Arg Tyr

```
<210> SEQ ID NO 13
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 13
```

Pro Lys Pro Glu Ala Pro Gly Lys Asp Ala Ser Pro Glu Glu Trp Asn
1               5                   10                  15

Arg Tyr Tyr Ala Ser Leu Arg His Tyr Leu Asn Trp Val Thr Arg Gln
            20                  25                  30

Arg Tyr

```
<210> SEQ ID NO 14
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 14
```

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Trp Val Thr Arg Gln
            20                  25                  30

Arg Tyr

```
<210> SEQ ID NO 15
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 15
```

Pro Lys Pro Glu His Pro Gly Lys Asp Ala Ser Pro Glu Glu Trp Asn

```
                1               5                  10                 15
Arg Tyr Tyr Ala Ala Leu Arg Lys Tyr Leu Asn Trp Val Thr Arg Gln
                20                  25                 30

Arg Tyr

<210> SEQ ID NO 16
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 16

Pro Lys Pro Glu His Pro Gly Lys Asp Ala Ser Pro Glu Glu Leu Asn
1               5                  10                 15

Lys Tyr Tyr Ala Ala Leu Arg His Tyr Leu Asn Trp Val Thr Arg Gln
                20                  25                 30

Arg Tyr

<210> SEQ ID NO 17
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 17

Pro Lys Pro Glu His Pro Gly Lys Asp Ala Ser Pro Glu Glu Leu Asn
1               5                  10                 15

Arg Tyr Tyr Ala Ser Leu Arg His Tyr Ile Asn Trp Val Thr Arg Gln
                20                  25                 30

Arg Tyr

<210> SEQ ID NO 18
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 18

Pro Lys Pro Glu His Pro Gly Lys Asp Ala Ser Pro Glu Glu Leu Ala
1               5                  10                 15

Arg Tyr Tyr Ala Ser Leu Arg His Tyr Leu Asn Trp Val Thr Arg Gln
                20                  25                 30

Arg Tyr

<210> SEQ ID NO 19
<211> LENGTH: 34
<212> TYPE: PRT
<213> ORGANISM: Artificial Sequence
<220> FEATURE:
```

```
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 19

Pro Lys Pro Glu His Pro Gly Lys Asp Ala Ser Pro Glu Glu Trp Asn
1               5                   10                  15

Arg Tyr Tyr Ala Ser Leu Arg His Tyr Ile Asn Trp Val Thr Arg Gln
            20                  25                  30

Arg Tyr

<210> SEQ ID NO 20
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 20

Pro Lys Pro Glu His Pro Gly Lys Asp Ala Ser Pro Glu Glu Trp Asn
1               5                   10                  15

Arg Tyr Tyr Ala Asp Leu Arg His Tyr Ile Asn Trp Val Thr Arg Gln
            20                  25                  30

Arg Tyr

<210> SEQ ID NO 21
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 21

Pro Lys Pro Glu His Pro Gly Lys Asp Ala Ser Pro Glu Glu Trp Asn
1               5                   10                  15

Arg Tyr Tyr Ala Asp Leu Arg His Tyr Leu Asn Trp Val Thr Arg Gln
            20                  25                  30

Arg Tyr

<210> SEQ ID NO 22
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 22

Pro Lys Pro Glu Ser Pro Gly Lys Asp Ala Ser Pro Glu Glu Trp Asn
1               5                   10                  15

Arg Tyr Tyr Ala Asp Leu Arg His Tyr Ile Asn Trp Val Thr Arg Gln
            20                  25                  30
```

```
<210> SEQ ID NO 23
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 23

Pro Lys Pro Glu Ser Pro Gly Lys Asp Ala Ser Pro Glu Glu Trp Asn
1               5                   10                  15

Arg Tyr Tyr Ala Asp Leu Arg His Tyr Leu Asn Trp Val Thr Arg Gln
            20                  25                  30

Arg Tyr

<210> SEQ ID NO 24
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 24

Pro Lys Pro Glu His Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 25
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 25

Pro Lys Pro Glu His Pro Gly Lys Asp Ala Ser Pro Glu Glu Trp Ala
1               5                   10                  15

Lys Tyr Tyr Ala Ala Leu Arg His Tyr Ile Asn Trp Val Thr Arg Gln
            20                  25                  30

Arg Tyr

<210> SEQ ID NO 26
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
```

<223> OTHER INFORMATION: AMIDATION

<400> SEQUENCE: 26

Pro Lys Pro Glu Ala Pro Gly Lys Asp Ala Ser Pro Glu Glu Trp Asn
1               5                   10                  15

Arg Tyr Tyr Ala Asp Leu Arg His Tyr Ile Asn Trp Val Thr Arg Gln
            20                  25                  30

Arg Tyr

<210> SEQ ID NO 27
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 27

Pro Lys Pro Glu His Pro Gly Lys Asp Ala Ser Pro Glu Glu Trp Asn
1               5                   10                  15

Arg Tyr Tyr Ala Ser Leu Arg Lys Tyr Leu Asn Trp Val Thr Arg Gln
            20                  25                  30

Arg Tyr

<210> SEQ ID NO 28
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 28

Pro Lys Pro Glu His Pro Gly Lys Asp Ala Ser Ala Glu Glu Trp Ala
1               5                   10                  15

Lys Tyr Tyr Ala Ala Leu Arg His Tyr Ile Asn Trp Val Thr Arg Gln
            20                  25                  30

Arg Tyr

<210> SEQ ID NO 29
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 29

Pro Lys Pro Glu Ala Pro Gly Lys Asp Ala Ser Ala Glu Glu Trp Asn
1               5                   10                  15

Arg Tyr Tyr Ala Ser Leu Arg His Tyr Leu Asn Trp Val Thr Arg Gln
            20                  25                  30

Arg Tyr

```
<210> SEQ ID NO 30
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 30

Pro Lys Pro Glu His Pro Gly Lys Asp Ala Ser Ala Glu Glu Leu Ala
1               5                   10                  15

Arg Tyr Tyr Ala Ser Leu Arg His Tyr Leu Asn Trp Val Thr Arg Gln
            20                  25                  30

Arg Tyr

<210> SEQ ID NO 31
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 31

Pro Lys Pro Glu Ala Pro Gly Lys Asp Ala Ser Ala Glu Glu Trp Asn
1               5                   10                  15

Arg Tyr Tyr Ala Ser Leu Arg Lys Tyr Leu Asn Trp Val Thr Arg Gln
            20                  25                  30

Arg Tyr

<210> SEQ ID NO 32
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 32

Pro Lys Pro Glu Ser Pro Gly Lys Asp Ala Ser Ala Glu Glu Trp Thr
1               5                   10                  15

Lys Tyr Tyr Ala Ala Leu Arg His Tyr Ile Asn Trp Val Thr Arg Gln
            20                  25                  30

Arg Tyr

<210> SEQ ID NO 33
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 33
```

Pro Lys Pro Glu Ala Pro Gly Lys Asp Ala Ser Pro Glu Glu Leu Asn
1               5                   10                  15

Arg Tyr Tyr Ala Ser Leu Arg Lys Tyr Leu Asn Trp Val Thr Arg Gln
            20                  25                  30

Arg Tyr

<210> SEQ ID NO 34
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 34

Pro Lys Pro Glu His Pro Gly Glu Asp Ala Ser Pro Glu Glu Trp Ala
1               5                   10                  15

Lys Tyr Tyr Ala Ala Leu Arg His Tyr Ile Asn Trp Val Thr Arg Gln
            20                  25                  30

Arg Tyr

<210> SEQ ID NO 35
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 35

Pro Lys Pro Glu Ala Pro Gly Glu Asp Ala Ser Ala Glu Glu Trp Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 36
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 36

Pro Lys Pro Glu Ser Pro Gly Glu Asp Ala Ser Pro Glu Glu Trp Thr
1               5                   10                  15

Lys Tyr Tyr Ala Ala Leu Arg His Tyr Ile Asn Trp Val Thr Arg Gln
            20                  25                  30

Arg Tyr

<210> SEQ ID NO 37
<211> LENGTH: 34
<212> TYPE: PRT
<213> ORGANISM: Artificial Sequence

```
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 37

Pro Lys Pro Glu Ala Pro Gly Glu Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 38
<211> LENGTH: 34
<212> TYPE: PRT
<213> ORGANISM: Artificial Sequence
<220> FEATURE:
<223> OTHER INFORMATION: PYY ANALOG

<400> SEQUENCE: 38

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 39
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (8)..(8)
<223> OTHER INFORMATION: Residue is modified as illustrated in
      specification.
<220> FEATURE:
<221> NAME/KEY: MOD_RES
<222> LOCATION: (34)..(34)
<223> OTHER INFORMATION: AMIDATION

<400> SEQUENCE: 39

Pro Lys Pro Glu Ala Pro Gly Cys Asp Ala Ser Ala Glu Glu Trp Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 40
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (8)..(8)
<223> OTHER INFORMATION: Residue is modified as illustrated in
      specification.
<220> FEATURE:
<221> NAME/KEY: MOD_RES
<222> LOCATION: (34)..(34)
<223> OTHER INFORMATION: AMIDATION
```

<400> SEQUENCE: 40

Pro Lys Pro Glu His Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 41
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (8)..(8)
<223> OTHER INFORMATION: Residue is modified as illustrated in
      specification.
<220> FEATURE:
<221> NAME/KEY: MOD_RES
<222> LOCATION: (34)..(34)
<223> OTHER INFORMATION: AMIDATION

<400> SEQUENCE: 41

Pro Lys Pro Glu His Pro Gly Lys Asp Ala Ser Pro Glu Glu Leu Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 42
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (8)..(8)
<223> OTHER INFORMATION: Residue is modified as illustrated in
      specification.
<220> FEATURE:
<221> NAME/KEY: MOD_RES
<222> LOCATION: (34)..(34)
<223> OTHER INFORMATION: AMIDATION

<400> SEQUENCE: 42

Pro Lys Pro Glu Ser Pro Gly Lys Asp Ala Ser Pro Glu Glu Trp Thr
1               5                   10                  15

Lys Tyr Tyr Ala Ala Leu Arg His Tyr Ile Asn Trp Val Thr Arg Gln
            20                  25                  30

Arg Tyr

<210> SEQ ID NO 43
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (8)..(8)
<223> OTHER INFORMATION: Residue is modified as illustrated in
      specification.
<220> FEATURE:
<221> NAME/KEY: MOD_RES
<222> LOCATION: (34)..(34)

<223> OTHER INFORMATION: AMIDATION

<400> SEQUENCE: 43

Pro Lys Pro Glu His Pro Gly Lys Asp Ala Ser Pro Glu Glu Trp Ala
1               5                   10                  15

Lys Tyr Tyr Ala Ala Leu Arg His Tyr Ile Asn Trp Val Thr Arg Gln
            20                  25                  30

Arg Tyr

<210> SEQ ID NO 44
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (8)..(8)
<223> OTHER INFORMATION: Residue is modified as illustrated in
      specification.
<220> FEATURE:
<221> NAME/KEY: MOD_RES
<222> LOCATION: (34)..(34)
<223> OTHER INFORMATION: AMIDATION

<400> SEQUENCE: 44

Pro Lys Pro Glu His Pro Gly Cys Asp Ala Ser Pro Glu Glu Trp Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 45
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (8)..(8)
<223> OTHER INFORMATION: Residue is modified as illustrated in
      specification.
<220> FEATURE:
<221> NAME/KEY: MOD_RES
<222> LOCATION: (34)..(34)
<223> OTHER INFORMATION: AMIDATION

<400> SEQUENCE: 45

Pro Lys Pro Glu His Pro Gly Cys Asp Ala Ser Pro Glu Glu Trp Ala
1               5                   10                  15

Lys Tyr Tyr Ala Ala Leu Arg His Tyr Ile Asn Trp Val Thr Arg Gln
            20                  25                  30

Arg Tyr

<210> SEQ ID NO 46
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 46

```
Pro Lys Pro Glu Ala Pro Gly Cys Asp Ala Ser Pro Glu Glu Trp Asn
1               5                   10                  15

Arg Tyr Tyr Ala Ser Leu Arg Lys Tyr Leu Asn Trp Val Thr Arg Gln
            20                  25                  30

Asn Tyr

<210> SEQ ID NO 47
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 47

Ile Lys Pro Glu Ala Pro Leu Ser Lys Gln Leu Glu Glu Glu Ala Val
1               5                   10                  15

Arg Tyr Tyr Ala Ser Leu Arg His Tyr Leu Asn Leu Val Thr Arg Gln
            20                  25                  30

Arg Tyr

<210> SEQ ID NO 48
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 48

Pro Lys Pro Glu Ala Pro Gly Glu Asp Ala Ser Pro Lys Glu Trp Asn
1               5                   10                  15

Arg Tyr Tyr Ala Ser Leu Arg Lys Tyr Leu Asn Trp Val Thr Arg Gln
            20                  25                  30

Arg Tyr

<210> SEQ ID NO 49
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 49

Pro Lys Pro Glu His Pro Gly Glu Asp Ala Ser Pro Glu Glu Leu Asn
1               5                   10                  15

Arg Tyr His Ala Ala Leu Arg Ala Tyr Leu Asn Leu Val Thr Arg Gln
            20                  25                  30

Arg Tyr

<210> SEQ ID NO 50
<211> LENGTH: 34
<212> TYPE: PRT
```

```
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 50

Pro Lys Pro Glu His Pro Gly Glu Asp Ala Ser Pro Glu Glu Leu Asn
1               5                   10                  15

Arg Tyr Tyr Ala Ala Leu Arg Ala Tyr Leu Asn Leu Val Thr Arg Gln
            20                  25                  30

Lys Tyr

<210> SEQ ID NO 51
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 51

Pro Lys Pro Glu His Pro Gly Glu Asp Ala Ser Pro Glu Glu Leu Asn
1               5                   10                  15

Arg Tyr Tyr Ala Ala Leu Arg Ala Tyr Leu Asn Leu Val Thr Lys Gln
            20                  25                  30

Arg Tyr

<210> SEQ ID NO 52
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 52

Pro Gln Pro Glu Ser Pro Gly Cys Asn Ala Ser Pro Glu Glu Leu Ala
1               5                   10                  15

Lys Tyr His Ala Ala Leu Arg His Tyr Val Asn Leu Ile Thr Arg Gln
            20                  25                  30

Arg Tyr

<210> SEQ ID NO 53
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 53

Ile Lys Pro Pro Tyr Pro Gly Cys Asp Ala Ser Pro Glu Glu Gln Asn
1               5                   10                  15
```

Lys Tyr Tyr Ala Ser Leu Arg Ala Tyr Trp Asn Leu Val Thr Arg Gln
            20                  25                  30

Arg Tyr

<210> SEQ ID NO 54
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 54

Pro Lys Pro Glu Ser Pro Gly Ser Asn Ala Ser Pro Glu Asp Trp Ala
1               5                   10                  15

Lys Tyr Gln Ala Ala Val Arg His Tyr Val Asn Leu Ile Thr Arg Gln
            20                  25                  30

Arg Tyr

<210> SEQ ID NO 55
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 55

Pro Glu Pro Glu His Pro Gly Cys Asp Ala Ser Pro Glu Asp Gln Asn
1               5                   10                  15

Lys Tyr His Ala Ser Leu Arg Lys Tyr Leu Asn Trp Val Thr Arg Gln
            20                  25                  30

Arg Tyr

<210> SEQ ID NO 56
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 56

Ile Lys Pro Pro Glu Pro Gly Cys Asp Ala Ser Pro Glu Glu Gln Asn
1               5                   10                  15

Lys Tyr Tyr Ala Ser Leu Arg His Tyr Trp Asn Leu Val Thr Arg Gln
            20                  25                  30

Arg Tyr

<210> SEQ ID NO 57
<211> LENGTH: 34
<212> TYPE: PRT
<213> ORGANISM: Artificial Sequence
<220> FEATURE:
<223> OTHER INFORMATION: PYY ANALOG
<220> FEATURE:

```
<221> NAME/KEY: MOD_RES
<222> LOCATION: (34)..(34)
<223> OTHER INFORMATION: AMIDATION

<400> SEQUENCE: 57

Ile Glu Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 58
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 58

Pro Lys Pro Glu Ser Pro Gly Ser Asp Ala Ser Pro Glu Asp Leu Ala
1               5                   10                  15

Lys Tyr His Ala Ala Val Arg His Tyr Val Asn Leu Ile Thr Arg Gln
            20                  25                  30

Arg Tyr

<210> SEQ ID NO 59
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 59

Pro Lys Pro Glu Ala Pro Gly Cys Asp Ala Ser Pro Glu Glu Trp Asn
1               5                   10                  15

Arg Tyr Tyr Ala Ser Leu Arg Lys Tyr Leu Asn Trp Val Thr Arg Gln
            20                  25                  30

His Tyr

<210> SEQ ID NO 60
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 60

Pro Lys Pro Val Ala Pro Gly Cys Asp Ala Ser Pro Ala Glu Leu Asn
1               5                   10                  15

Arg Gln Tyr Ser Asp Leu Arg Asn Tyr Trp Asn Leu Val Thr Arg Gln
            20                  25                  30

Arg Tyr
```

<210> SEQ ID NO 61
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 61

Ile Gln Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 62
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 62

Pro Lys Pro Glu Ser Pro Gly Lys Asp Ala Ser Pro Glu Asp Leu Ala
1               5                   10                  15

Lys Tyr His Ala Ala Val Arg His Tyr Val Asn Leu Ile Thr Arg Gln
            20                  25                  30

Arg Tyr

<210> SEQ ID NO 63
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 63

Pro Gln Pro Glu Ser Pro Glu Gly Asn Ala Ser Pro Glu Asp Trp Ala
1               5                   10                  15

Cys Tyr His Ala Ala Val Arg His Tyr Val Asn Leu Ile Thr Arg Gln
            20                  25                  30

Arg Tyr

<210> SEQ ID NO 64
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

```
<400> SEQUENCE: 64

Ile His Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 65
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 65

Ile Lys Pro Glu Ala Pro Gly Glu Asp Ala Ser Pro Glu Gln Leu Met
1               5                   10                  15

Ala Gln Tyr Ala Ser Leu Arg His Tyr Leu Asn Leu Val Thr Arg Gln
            20                  25                  30

Arg Tyr

<210> SEQ ID NO 66
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 66

Pro Lys Pro Glu Ala Pro Leu Ser Lys Gln Leu Glu Glu Glu Ala Val
1               5                   10                  15

Arg Tyr Tyr Ala Ser Leu Arg His Tyr Leu Asn Leu Val Thr Arg Gln
            20                  25                  30

Arg Tyr

<210> SEQ ID NO 67
<211> LENGTH: 34
<212> TYPE: PRT
<213> ORGANISM: Artificial Sequence
<220> FEATURE:
<223> OTHER INFORMATION: PYY ANALOG
<220> FEATURE:
<221> NAME/KEY: MOD_RES
<222> LOCATION: (34)..(34)
<223> OTHER INFORMATION: AMIDATION

<400> SEQUENCE: 67

Pro Lys Pro Glu Ala Pro Gly Cys Asp Ala Ser Pro Glu Glu Leu Asn
1               5                   10                  15

Arg Tyr Gln Ala Ser Leu Arg His Tyr Leu Asn Leu Val Thr Arg Gln
            20                  25                  30

Arg Tyr
```